(12) United States Patent
Marnfeldt

(10) Patent No.: US 12,390,649 B2
(45) Date of Patent: *Aug. 19, 2025

(54) GRAPHICAL USER INTERFACE FOR ADJUSTING CURRENT MAGNITUDE IN A STIMULATOR DEVICE

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 18/351,146

(22) Filed: Jul. 12, 2023

(65) Prior Publication Data

US 2023/0355993 A1    Nov. 9, 2023

Related U.S. Application Data

(63) Continuation of application No. 17/185,436, filed on Feb. 25, 2021, now Pat. No. 11,745,021.

(Continued)

(51) Int. Cl.
*A61N 1/372*    (2006.01)
*A61N 1/05*    (2006.01)
*A61N 1/36*    (2006.01)

(52) U.S. Cl.
CPC ....... *A61N 1/37247* (2013.01); *A61N 1/0534* (2013.01); *A61N 1/0551* (2013.01); *A61N 1/36062* (2017.08)

(58) Field of Classification Search
CPC .............. A61N 1/37247; A61N 1/0534; A61N 1/0551; A61N 1/36062
See application file for complete search history.

(56) References Cited

U.S. PATENT DOCUMENTS 6,181,969 B1    1/2001    Gord
8,606,362 B2    12/2013    He et al.
(Continued)

FOREIGN PATENT DOCUMENTS

EP    2378402 A2    10/2011
WO    2014/036075    3/2014
(Continued)

OTHER PUBLICATIONS

Invitation to Pay Additional Fees regarding corresponding PCT Application No. PCT/US2021/019650, mailed Jun. 7, 2021.

(Continued)

*Primary Examiner* — Joseph M Dietrich
(74) *Attorney, Agent, or Firm* — Lewis & Reese, PLLC

(57) ABSTRACT

A Graphical User Interface (GUI) for an external device used to program an implantable stimulator device is disclosed. The GUI includes aspects useful in adjusting the current magnitude provided at one or more of the stimulator device's electrodes. In particular, the GUI includes an amplitude slider, which allows the user to slide an indicator to increase or decrease the current magnitude at different rates depending on the length of the slide. The GUI further allows the user to prescribe drop back functionality, which reduces the current magnitude by a prescribed amount when the indicator is released. In one example, drop back functionality can be engaged in accordance with a rate threshold, and thus drop back functionality will only occur when the rate of increase equals or is above the threshold when the control button is released.

20 Claims, 16 Drawing Sheets

Related U.S. Application Data

(60) Provisional application No. 63/000,114, filed on Mar. 26, 2020.

(56) References Cited

U.S. PATENT DOCUMENTS

| | | |
|---|---|---|
| 8,620,436 B2 | 12/2013 | Parramon et al. |
| 8,630,715 B2 | 1/2014 | Goetz et al. |
| 11,745,021 B2 * | 9/2023 | Marnfeldt ............ A61N 1/0534 607/60 |
| 2007/0203545 A1 | 8/2007 | Stone et al. |
| 2008/0319497 A1 | 12/2008 | Griffith et al. |
| 2009/0024189 A1 | 1/2009 | Lee et al. |
| 2012/0095529 A1 | 4/2012 | Parramon et al. |
| 2013/0289665 A1 | 10/2013 | Marnfeldt et al. |
| 2015/0080982 A1 | 3/2015 | Funderburk |
| 2015/0231402 A1 | 8/2015 | Aghassian |
| 2015/0360038 A1 | 12/2015 | Zottola et al. |
| 2016/0246935 A1 | 8/2016 | Cerny et al. |
| 2017/0021178 A1 | 1/2017 | Bradley et al. |
| 2018/0071512 A1 | 3/2018 | Feldman et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0140831 A1 | 5/2018 | Feldman et al. |
| 2019/0083796 A1 | 3/2019 | Weerakoon et al. |
| 2019/0126030 A1 | 5/2019 | Cheeran et al. |
| 2019/0175915 A1 | 6/2019 | Brill et al. |
| 2021/0275798 A1 | 9/2021 | Marnfeldt |
| 2022/0184399 A1 | 6/2022 | Zhang et al. |

FOREIGN PATENT DOCUMENTS

| | | |
|---|---|---|
| WO | 2018/163060 | 9/2018 |
| WO | 2019/195320 | 10/2019 |
| WO | 2020/223165 | 11/2020 |

OTHER PUBLICATIONS

International Search Report and Written Opinion regarding corresponding PCT Application No. PCT/US2021/019650, mailed Jul. 28, 2021.

Communication Pursuant to Article 94(3) EPC regarding corresponding European Patent Application No. 21712682.0, mailed Oct. 24, 2024.

* cited by examiner

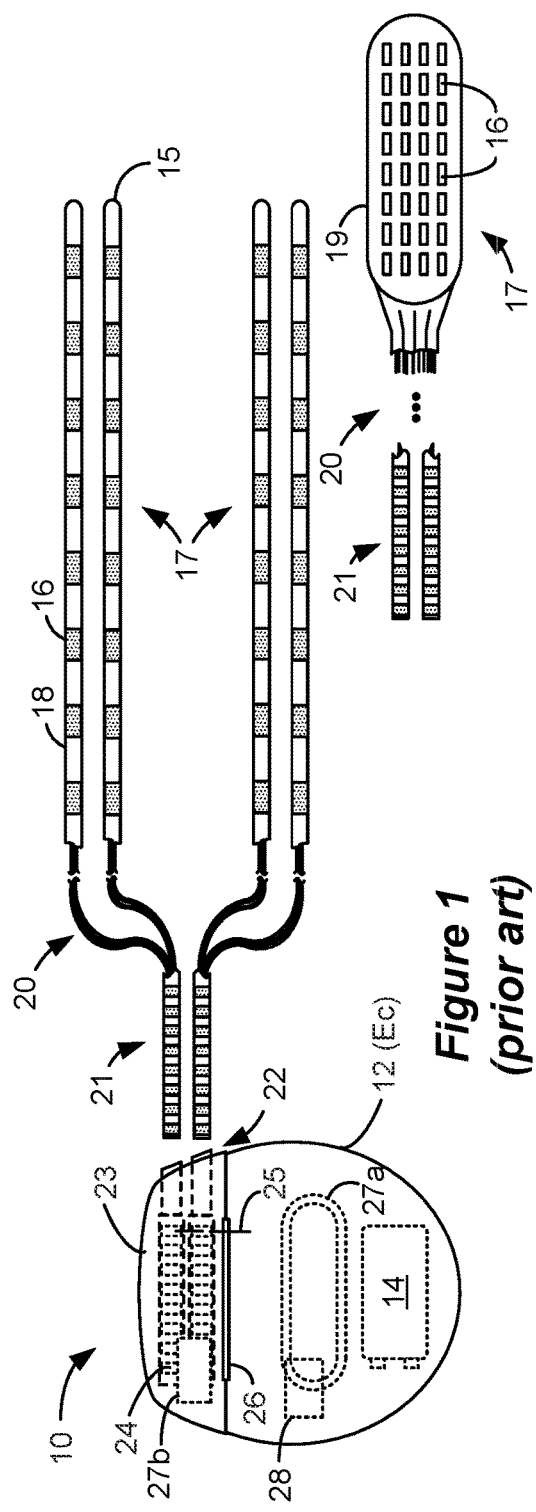
*Figure 1 (prior art)*
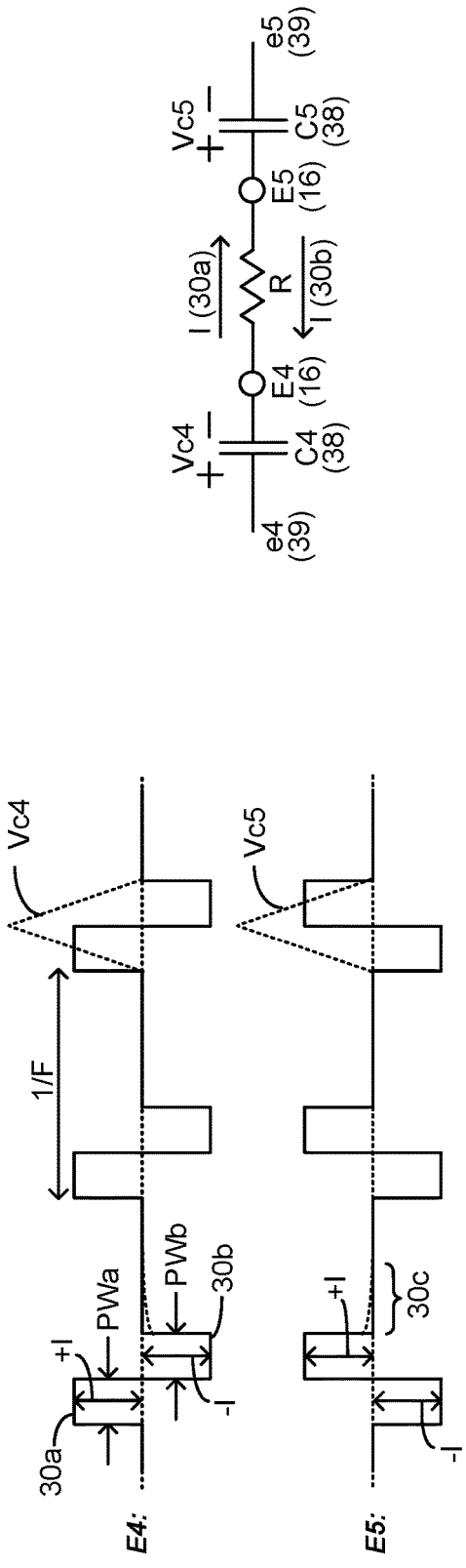
*Figure 2A (prior art)*
*Figure 2B (prior art)*

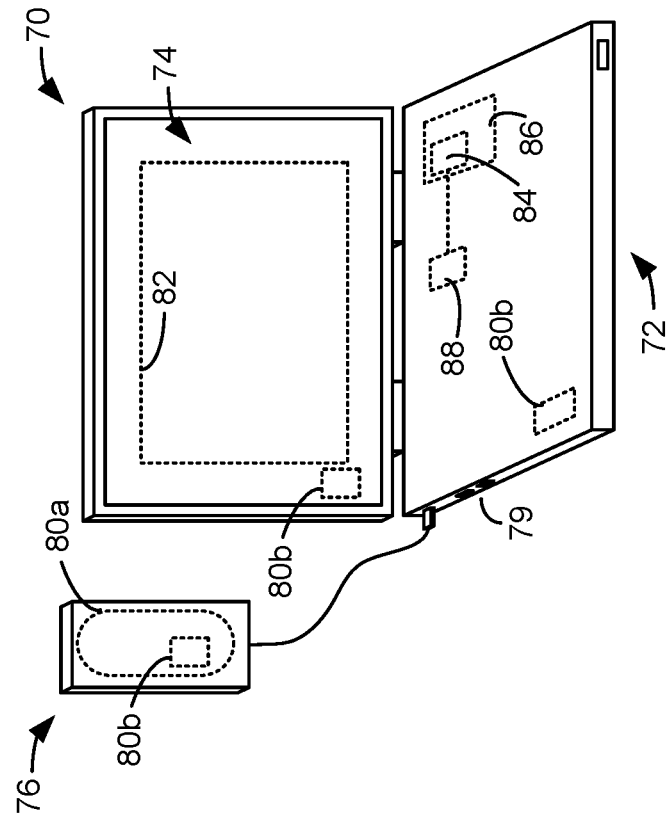
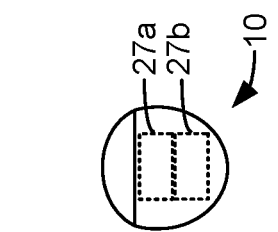
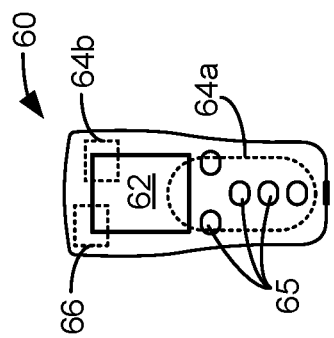
Figure 5A (prior art)

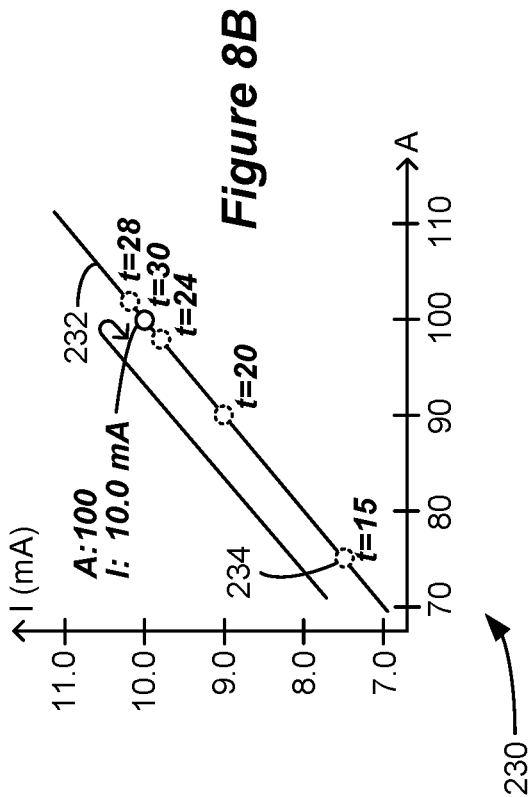
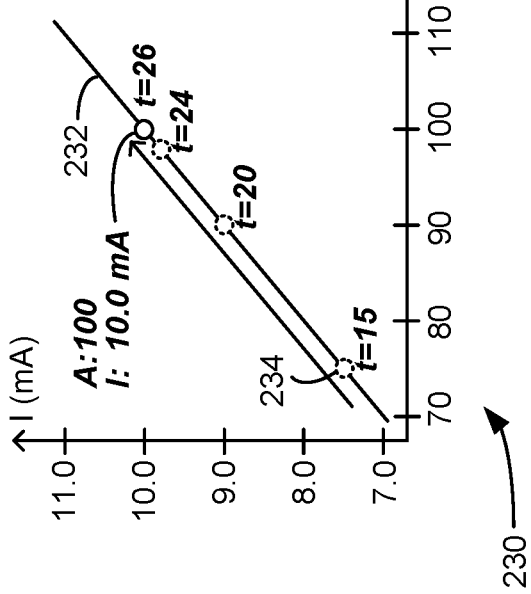
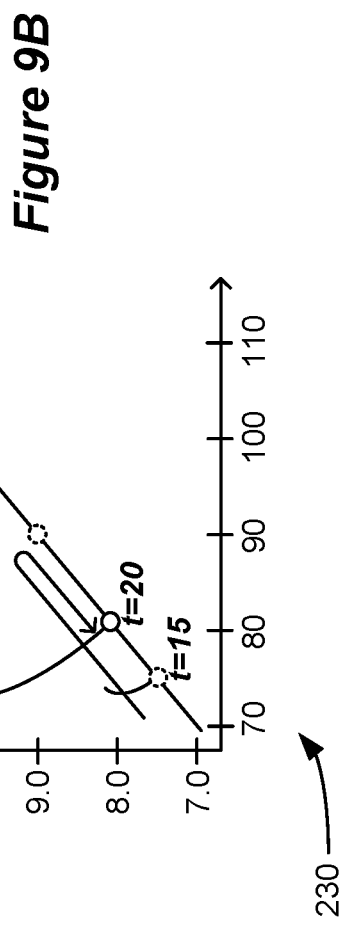

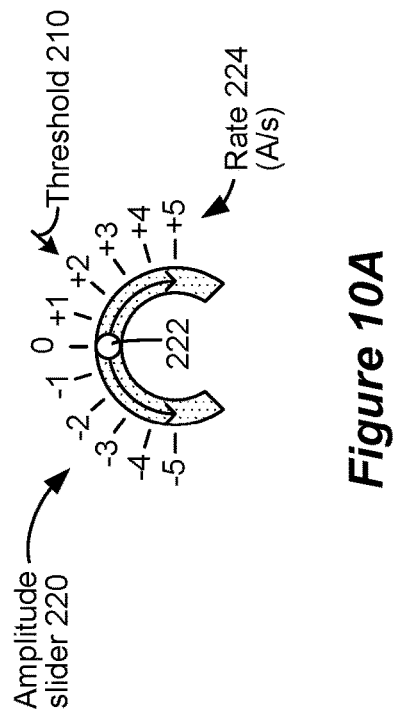
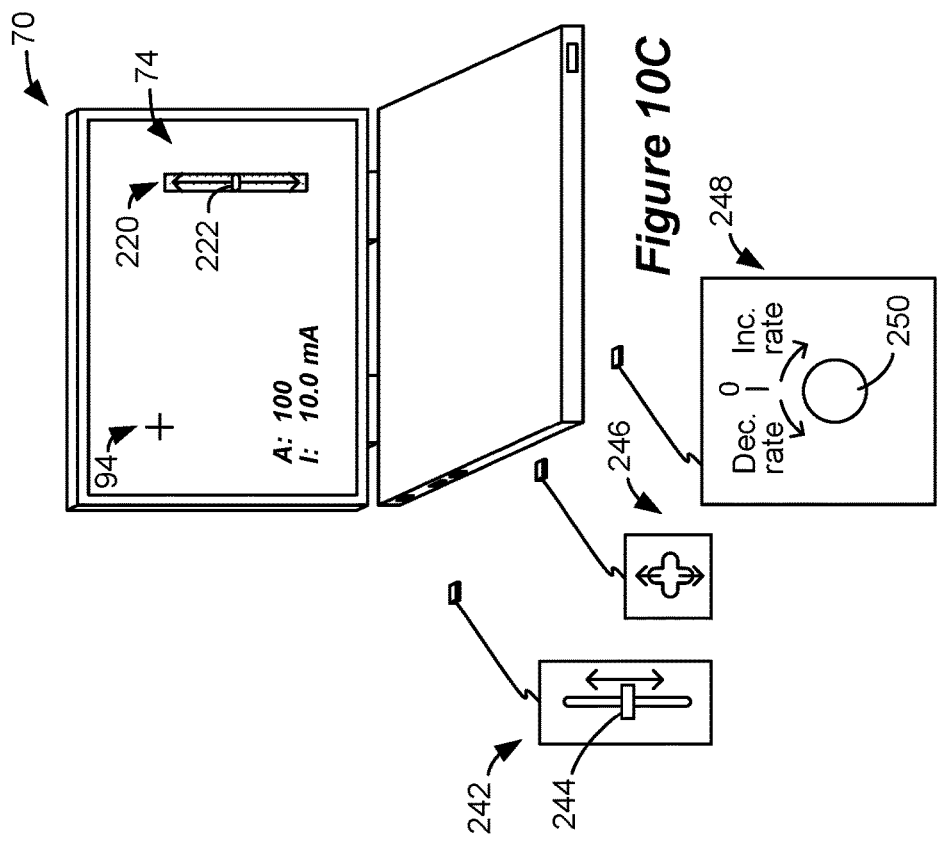

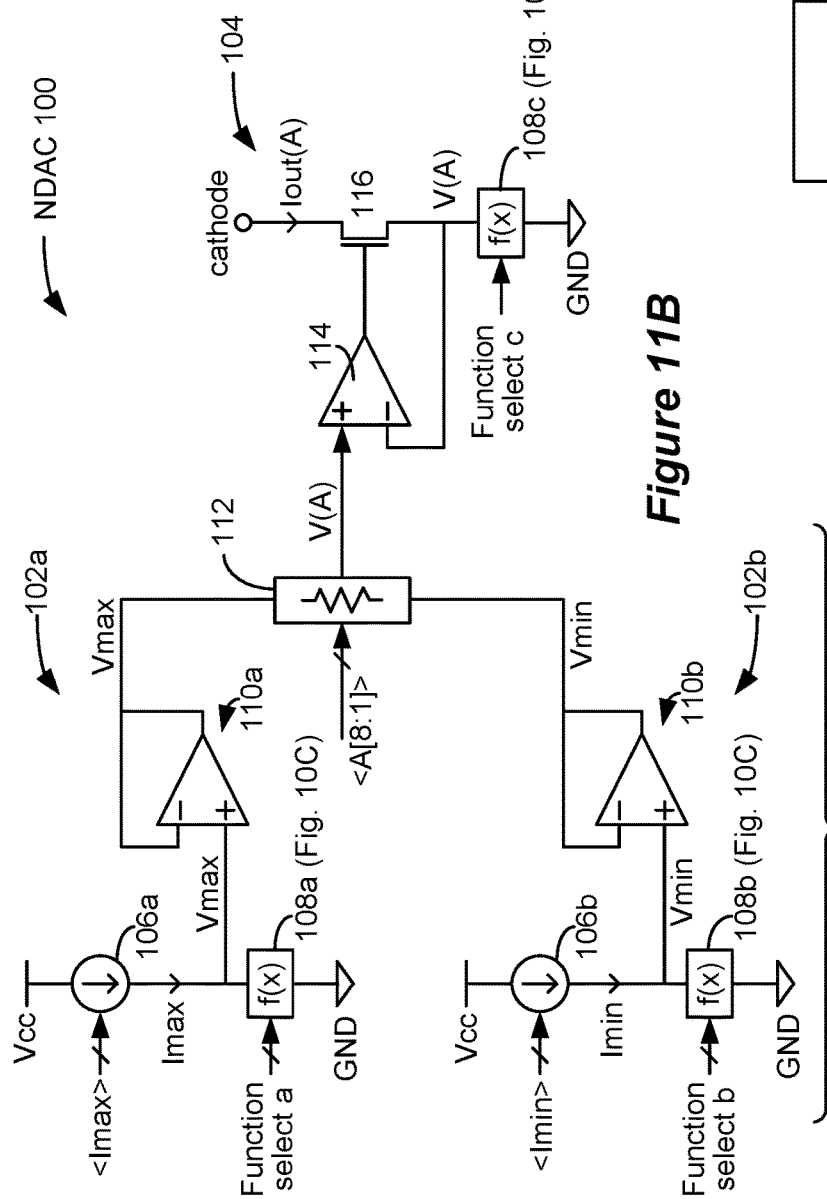
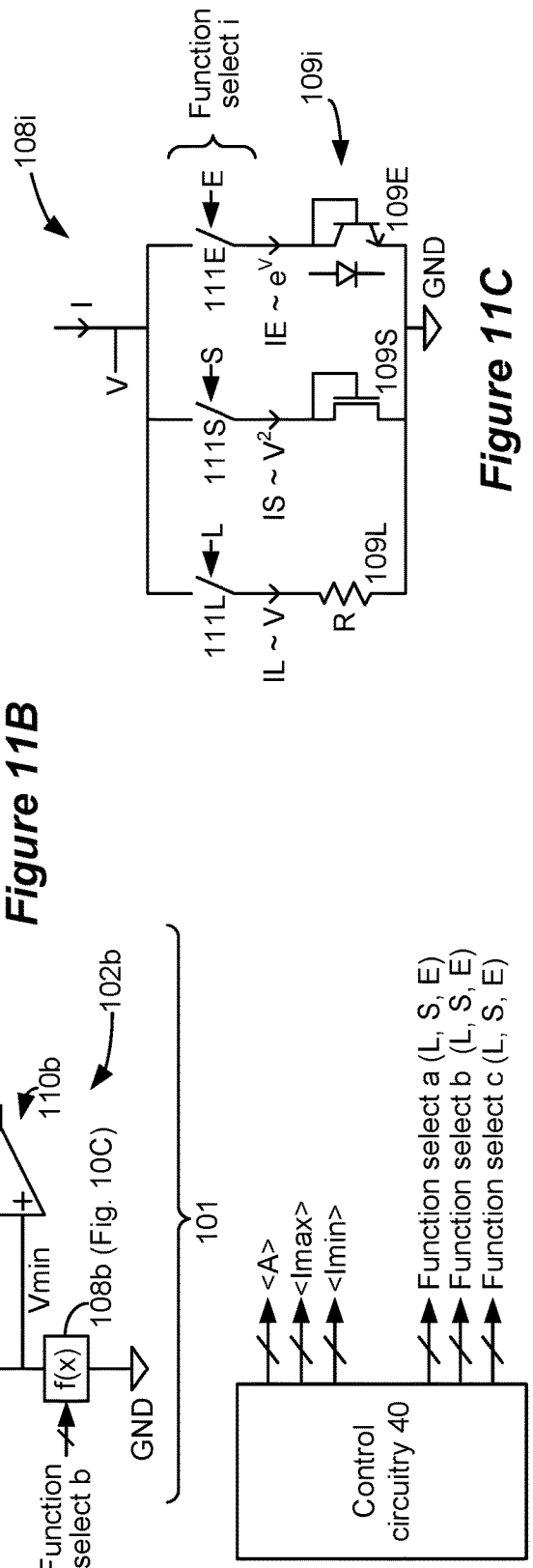
*Figure 11B*
*Figure 11C*

GRAPHICAL USER INTERFACE FOR ADJUSTING CURRENT MAGNITUDE IN A STIMULATOR DEVICE

CROSS REFERENCE TO RELATED APPLICATIONS

This is a continuation application of U.S. patent application Ser. No. 17/185,436, filed Feb. 25, 2021, which is a non-provisional of U.S. Provisional Patent Application Ser. No. 63/000,114, filed Mar. 26, 2020. These applications are incorporated herein by reference in their entireties, and priority is claimed to them.

FIELD OF THE INVENTION

This application relates to implantable stimulator device systems, and in particular to external communication devices including user interfaces to control the stimulation provided at the electrodes of the device.

INTRODUCTION

Implantable neurostimulator devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system or a Deep Brain Stimulation (DBS) system. However, the present invention may find applicability with any implantable neurostimulator device system.

An SCS or DBS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, lead connectors, and electrodes in an IPG is application-specific and therefore can vary. The conductive case 12 can also comprise an electrode (Ec). In a SCS application, the electrode lead(s) are typically implanted in the spinal column proximate to the dura in a patient's spinal cord, and the IPG is typically implanted under the skin in the buttocks region. In a DBS application, the electrode leads are typically implanted in particular regions of the brain, and the IPG is typically implanted under the skin under the clavicle (collarbone). In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of neurostimulation therapy is to provide electrical stimulation from the electrodes 16 to alleviate a patient's symptoms, such as chronic back pain in an SCS application, or tremors in a DBS application.

IPG 10 can include an antenna 27a allowing it to communicate bi-directionally with a number of external devices used to program or monitor the IPG, such as a hand-held patient remote control 60 or a clinician programmer 70, which are explained later with reference to FIGS. 5A and 5B. Antenna 27a comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b, which is shown within the header 23, but may also be within the case 12. RF antenna 27b may comprise a patch, slot, or wire, and may operate as a monopole or dipole. RF antenna 27b preferably communicates with external devices using far-field electromagnetic waves, and may operate in accordance with any number of known RF communication standards, such as Bluetooth, Zigbee, MICS, and the like. If the battery 14 is rechargeable, the IPG 10 may further include a charging coil (not shown) to wirelessly receive energy from an external charging device. Further details concerning external devices in an implantable stimulation system can be found for example in U.S. Patent Application Publications 2015/0360038 and 2015/0231402.

Stimulation in IPG 10 is typically provided by pulses, and each pulse may include a number of phases, as shown in the example of FIG. 2A. Stimulation parameters for the pulses typically include magnitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of magnitude +I to the tissue. Electrode E5 has been selected as a cathode (again during first phase 30a), and thus provides pulses which sink a corresponding negative current of magnitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3A shows an example of stimulation circuitry 28, which includes Digital-to-Analog converters (DACs) that provide analog currents at the electrodes in accordance with specified magnitudes as explained further below. The stimulation circuitry 28 depicted includes a plurality of current source circuits (PDACs) and a plurality of current sink circuits (NDACs), so named in accordance with the Positive (sourced, anodic) and Negative (sunk, cathodic) currents they respectively issue. In the example shown, a NDACi/PDACi pair is dedicated (hardwired) to a particular electrode node ei, each of which is connected to one of the electrodes Ei 16 via DC-blocking capacitors Ci 38, for the reasons explained below. The stimulation circuitry 28 in this example also supports selection of the conductive case 12 as an electrode (Ec 12), which case electrode is typically selected for monopolar stimulation. While the PDACs and NDACs are assumed in this disclosure to comprise current sources able to provide a prescribed constant current, they can also comprise voltage sources able to provide a prescribed constant voltage.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter or can comprise a capacitor-based charge pump, as explained in U.S. Patent Application Publication 2018/0071512 for example. Because the resistance of the tissue is variable, VH may also be variable, and can be as high as 18 Volts in one example. Although not shown, U.S. Patent Application Publications 2018/0071520 explains that the PDACs and the NDACs can be powered by different power supply domains. For example, the PDACs can be powered using a first power supply domain, which includes VH as the high supply and VH-Vcc as the low supply (both of which may vary, because VH may vary). The NDACs can be powered using a second power supply domain, which includes Vcc as the high supply and ground (GND) as the low supply.

Proper control of the stimulation circuitry 28 allows any of the electrodes 16 to act as an anode or a cathode to create a current through a patient's tissue, R, hopefully with good therapeutic effect. The magnitude of the current provided by each NDACi is controlled via a digital amplitude bus <Ani>, thus allowing its associated electrode Ei to act as a cathode electrode to sink a current of the prescribed magnitude from the tissue. Likewise, the magnitude of the current provided by each PDACi is controlled via a digital amplitude bus <Api>, thus allowing its associated electrode Ei to act as an anode electrode to source a current of the prescribed magnitude to the tissue.

The digital amplitude buses <Ani> and <Api>, as well as other digital control signals for the DACs, can be issued by digital control circuitry 40 in the IPG 10. Digital control circuitry 40 can comprise a microcontroller, such as Part Number MSP430, manufactured by Texas Instruments, which is described in data sheets at http://www.ti.com/lsds/ti/microcontroller/16-bit_msp430/overview.page?DCMP=MCU_other& HQS=msp430. Control circuitry 40 more generally can comprise a microprocessor, Field Programmable Grid Array, Programmable Logic Device, Digital Signal Processor or like devices, and may include a central processing unit capable of executing instructions, with such instructions stored in volatile or non-volatile memory within or associated with the control circuitry. Digital control circuitry 40 can be separate from the stimulation circuitry 28; for example each may be formed in their own integrated circuits. Alternatively, the digital control circuitry 40 and stimulation circuitry 28 may also be integrated on the same integrated circuit, such as an Application Specific Integrated Circuit (ASIC). Various examples of digital control circuitry 40 and stimulation circuitry 28, and how they can be connected or integrated, are provided in U.S. Patent Application Publications 2008/0319497, 2012/0095529, 2018/0071513, 2018/0071520, or 2019/0083796, which are incorporated herein by reference in their entireties.

FIG. 3A shows programming of the stimulation circuitry 28 as necessary to create the first phase 30a of FIG. 2A, in which electrodes E4 and E5 are selected as an anode and cathode respectively to create a current of magnitude I through the tissue. In this example, digital amplitude bus <Ap4> serving PDAC4 is set with amplitude value X corresponding to the desired current magnitude I, as is bus <An5> servicing NDAC5. These buses would be asserted at particular times to produce the desired current, I, with the correct timing (e.g., in accordance with the prescribed frequency F and pulse width PWa). During the second phase 30b (PWb), PDAC5 and NDAC4 would be similarly programmed via digital amplitude buses <Ap5> and <An4> to reverse the polarity of the current, as is useful during the production of biphasic pulses, discussed further below. Other digital amplitude buses used to program PDACs and NDACs associated with other non-active electrodes (e.g., <Ap1> and <An1> associated with PDAC1 and NDAC1 at electrode E1) would be set to zero, or these PDACs or NDACs could be inactivated by other means. More than one anode electrode and more than one cathode electrode may be selected at one time through appropriate control of the DACs, and thus current can flow through the tissue R between two or more of the electrodes 16.

Also shown in FIG. 3A are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS is typically used after an electrode array 17 has been implanted in the patient. The proximal ends of the leads in the electrode array 17 pass through an incision in the patient and are connected to the externally-worn ETS, thus allowing the ETS to provide stimulation to the patient during the trial period. An ETS can include various antennas for communicating with external devices, similarly to the IPG 10. Further details concerning an ETS device are described in U.S. Pat. No. 9,259,574 and U.S. Patent Application Publication 2019/0175915. For purposes of this disclosure, an ETS comprises a type of implantable stimulator device.

Referring again to FIG. 2A, the stimulation pulses as shown are biphasic, with each pulse at each electrode comprising a first phase 30a followed thereafter by a second phase 30b of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same magnitude (|+I|=|−I|) for each of the pulse phases 30a and 30b. However, the pulse phases 30a and 30b may also be charged balance if the product of the magnitude and pulse widths of the two phases 30a and 30b are equal, as is known.

FIG. 3A shows that stimulation circuitry 28 can include passive recovery switches 41i, which are described further in U.S. Patent Application Publications 2018/0071527 and 2018/0140831. Passive recovery switches 41i may be attached to each of the electrode nodes 39, and are used to passively recover any remaining charge, such as may remain on the DC-blocking capacitors Ci 38 after issuance of the second pulse phase 30b. Passive charge recovery occurs without actively driving a current using the DAC circuitry, and can be prudent, because non-idealities in the stimulation circuitry 28 may lead to active charge recovery that is not perfectly charge balanced. Passive charge recovery typically occurs during a phase 30c (FIG. 2A), which may comprise a portion of the quiet periods between the pulses, by closing passive recovery switches 41i connected to the electrode nodes 39 at one end. The other end of the switches 41i are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements in the output current paths by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b imparts a predominance of charge at a given electrode. Although not illustrated, control of the passive recovery switches can occur via signals output by the digital control circuitry 40.

Other designs for stimulation circuitries 28 can be used in the IPG 10, and FIG. 3A is just one example. In another example shown in FIG. 3B, PDACs and NDACs may not be dedicated to work with particular electrodes. Instead, a switching matrix (SM Pi) can intervene between each PDACi and the electrode nodes ei 39, and a switching matrix (SM Ni) can intervene between each NDACi and the electrode nodes ei 39. Each switching matrix can be controlled by a digital switch bus (e.g., <Sp1>, <Sn1>, etc.) to control the electrode node to which its associated DAC's output (e.g., PDAC1, NDAC1, etc.) should be connected. Depending on the design, and unlike what is shown in FIG. 3B, stimulation circuitry 28 may include only one PDAC (and one switching matrix SM P) and only one NDAC (and one switching matrix SM N). However, providing more than one PDAC and more than one NDAC (e.g., 'x' of each, as shown in FIG. 3B) allows for the formation of more complex stimulation, such as stimulation requiring the simultaneous control of the current at more than one anode or cathode electrode, or stimulation formed in different timing channels. In the example of FIG. 3B, the digital control circuitry 40 would issue the digital amplitude buses for each PDAC and NDAC (e.g., <Ap1>, <An1>, etc.), as well as the digital switch buses (e.g., <Sp1>, <Sn1>, etc.) for each switching matrix, in accordance with the stimulation program the IPG 10 is programmed to execute. Still other variations of stimulation circuitry 28 are possible, and different options are disclosed in U.S. Pat. Nos. 6,181,969, 8,606,362, 8,620, 436, and U.S. Patent Application Publications 2018/0071520 and 2019/0083796.

FIG. 4 shows example circuitry for a given NDAC and PDAC, such as those used in FIGS. 3A and 3B, although again the PDACs and NDACs can be built differently as the references just cited explain. The magnitude of the current output by the NDAC, as noted earlier, is controlled by a digital amplitude bus <An[8:1]>, which in this example comprises eight digital control signals An[8]-An[1] capable of representing 256 different amplitude values. Each of these digital control signals is input to a selection transistor 56n, each of which is in series with a differing number of transistors 54n connected in parallel. A reference current Iref is produced by a generator 50n, and is provided to a transistor 52n, which mirrors its current to each of the transistors 54n. (Such current mirroring occurs because the gates of transistor 52n and transistors 54n are connected to transistor 52n's drain, as is well known).

The number of parallelled transistors 54n varies in binary fashion, such that An[1] controls connection of one transistor 54n to provide Iref; An[2] controls connection of two transistors 54n which together provide 2*Iref; An[3] controls connection of four transistors 54n which together provide 4*Iref, and so on, with An[8] controlling connection of 128 transistors 54n which together provide 128*Iref. Because selection transistors 56n are N-channel transistors in this example, the digital control signals An[i] are preferably active high. Therefore, for example, if the digital amplitude bus <An[8:1]>='00110101', i.e., the number 53 in binary, control signals An[6], An[5], An[3], and An[1] are asserted to close their associated selection transistors 56n. These control signals respectively cause 32*Iref, 16*Iref, 4*Iref, and Iref to be sunk to the NDAC (e.g., either from the NDAC's associated electrode node (FIG. 3A) or to the NDAC's associated switch matrix (FIG. 3B)), for a total of 53*Iref. If it is assumed then that Iref=0.1 mA, the current Iout sunk would equal 5.3 mA. In short, by asserting various of the digital control signals in the digital amplitude bus <An[8:1]>, output currents Iout over a dynamic range from Iref=0.0 mA ('00000000') to 255*Iref=25.5 mA ('11111111') can be sunk to the NDAC in increments of Iref=0.1 mA. Iref could of course comprise a different magnitude than 0.1 mA, and amplitude An could comprise a different number of increments than 256.

The PDAC is largely similar in construction to the NDAC, although operating to source a current. Again, selection transistors 56p are controlled by digital amplitude bus <Ap[8:1]>, with each transistor 56p controlling the current from different numbers of paralleled transistors 54p. Iref as produced by a generator 50p is mirrored by a transistor 52p to the transistors 54p. Because selection transistors 56p are P-channel transistors, the digital control signals Ap[i] are preferably active low. Therefore, for example, if the digital amplitude bus <Ap[8:1]>='11001010', i.e., the complement of 53 in binary, control signals Ap[6], Ap[5], Ap[3], and An[1] are asserted to close their associated selection transistors 56p, which respectively cause 32*Iref, 16*Iref, 4*Iref, and Iref to be sourced for a total of 53*Iref. Assuming again that Iref=0.1 mA, the current Iout sourced (e.g., to the PDAC's electrode node (FIG. 3A) or switch matrix (FIG. 3B)) would equal 5.3 mA (Note that the Iref may be trimmable at generators 50p and 50n to ensure the currents produced by the PDAC and NDAC are properly balanced). Again, by asserting various of the digital control signals in the digital amplitude bus <Ap[8:1]>, output currents Iout over a dynamic range from Iref=0.0 mA ('11111111') to 255*Iref=25.5 mA ('00000000') can be sourced from the PDAC in 256 increments of Iref=0.1 mA.

FIG. 5A shows various external devices that can wirelessly communicate data with the IPG 10 (or an ETS), including a patient remote control 60, and a clinician programmer 70. Both of devices 60 and 70 can be used to wirelessly transmit a stimulation program to the IPG 10—that is, to program its stimulation circuitry 28 stimulation with a desired amplitude and timing, and at selected electrodes. Both devices 60 and 70 may also be used to adjust one or more stimulation parameters of a stimulation program that the IPG 10 is currently executing. Devices 60 and 70 may also wirelessly receive information from the IPG 10, such as various status information, etc.

Clinician programmer 70 is typically used by a clinician in a clinician setting (e.g., an operating room, or a clinician's office), and as a result the clinician programmer 70 typically includes sophisticated functionality when compared to the simpler patient remote control 60. As described further in U.S. Patent Application Publication 2015/0360038, the clinician programmer 70 can comprise a computing device 72, such as a desktop, laptop, or notebook computer, a tablet, a mobile smart phone, a Personal Data Assistant (PDA)-type mobile computing device, etc. In FIG. 5A, computing device 72 is shown as a laptop computer that includes typical computer user interface means such as a screen 74, a mouse, a keyboard, speakers, a stylus, a printer, etc., not all of which are shown for convenience. Also shown in FIG. 5A are accessory devices for the clinician programmer 70 that are usually specific to its operation as a stimulation controller, such as a communication "wand" 76 coupleable to suitable ports on the computing device 72, such as USB ports 79 for example. If the patient's IPG 10 includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27b, the wand 76, the computing device 72, or both, can likewise include an RF antenna 80b to establish communication with the IPG 10 or ETS 50 at larger distances. The clinician programmer 70 can also communicate with other devices and networks, such as the Internet, either wirelessly or via a wired link provided at an Ethernet or network port.

To program stimulation programs or parameters for the IPG 10, the clinician interfaces with a clinician programmer GUI 82 provided on the screen 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by controller circuitry 88 such as one or more microprocessors, microcomputers, FPGAs, DSPs, other digital logic structures, etc., which are capable of executing programs in a computing device, and which may comprise their own memories. In one example, controller circuitry 88 may comprise an i5 processor manufactured by Intel Corp., as described at https://www.intel.com/content/www/us/en/products/processors/core/i5-processors.html. Such controller circuitry 88, in addition to executing the clinician programmer software 84 and rendering the GUI 82, can also enable communications via antennas 80a or 80b to communicate stimulation parameters chosen through the GUI 82 to the patient's IPG 10.

FIG. 5B shows further details of the GUI 82, which includes a leads interface 90 showing a depiction of the electrode array 17, perhaps with reference to its location within the patient (e.g., with reference to various vertebrae). The GUI 82 can further include a parameters interface 92 used to set various stimulation parameters, such as the current magnitude (I), pulse width (PW), and frequency (F) of the stimulation pulses. In reality the parameters interface 142 can be much more complicated, and can include many other options to define the stimulation to be provided. Selectable on-screen buttons 96 can be used to increase and decrease the values of the stimulation parameters, typically in fixed increments. A cursor 94, controllable by a mouse or other computer peripheral device, can be used to select positions in the electrode array 17 that will receive stimulation, and such positions can be designated as anode poles (e.g., 96a) which will source current to the tissue, or cathode poles (e.g., 96b) which will sink current from the tissue. The poles 96a and 96b can appear at the physical positions of particular electrodes 16, or virtual poles can be set at other random positions in the electrode array 17. As well as allowing a pole to be designated as an anode or cathode, the parameters interface 92 allows a user to specify a percentage X % of the current I that that electrode or pole is to receive. For example, FIG. 5A shows a tripole, with two anode poles 96a flanking a cathode pole 96b, and it may be assumed that the cathode pole 96b will receive 100% of the specified current I and so will sink −I, while the anodes poles 96a will share the specified current with each sourcing +0.5I. These details are explained further in U.S. Patent Application Publication 2022/0184399.

Referring again to FIG. 5A, the patient remote control 60 may generally provide similar functionality to the clinician programmer 70, and can include the same or similar hardware and software programming. For example, the external controller 60 includes control circuitry 66 similar to the controller circuitry 88 in the clinician programmer 70, and may similarly be programmed with software stored in device memory. However, given that the remote control 60 is a patient device, it may be simpler in design and thus lack certain features and functionality present in the more-powerful clinician programmer 70. For example, the remote control 60 may be used to adjust the magnitude of the stimulation, and in this regard can include options allowing the magnitude to be incremented or decremented, but may be unable to adjust other more-sophisticated stimulation parameters (e.g., the frequency and pulse width, the position of the stimulation poles in the electrode array, etc.).

As described in U.S. Patent Application Publication 2015/0080982, the patient remote control 60 may comprise a controller dedicated to work with the IPG 10. Remote control 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. The remote control 60 includes a GUI, which preferably includes a screen 62 and buttons 65 for entering commands and making various selections in the GUI's menu structure. Buttons 65 may also comprise selectable icons or links that are rendered on the screen 62, and the screen itself may comprise a touch screen, in which case buttons 65 may be unnecessary. The remote control 60 can have one or more antennas capable of communicating with the IPG 10. For example, the external controller 60 can have a near-field magnetic-induction coil antenna 64a capable of wirelessly communicating with the coil antenna 27a in the IPG 10, and/or a far-field RF antenna 64b capable of wirelessly communicating with the RF antenna 27b in the IPG 10.

SUMMARY

A method is disclosed for controlling an implantable stimulator device using an external device. The method may comprise: providing on a screen of the external device a graphical user interface (GUI), wherein the GUI includes a slider with an indicator; receiving at the GUI an input from a user to slide the indicator to adjust a rate at which a current magnitude is adjusted at one or more of the electrodes, wherein the rate is a function of a length that the indicator is slid; and providing the current magnitude as adjusted to the implantable stimulator device.

In one example, the indicator comprises an on-screen button configured to be selectable by the user to slide the indicator. In one example, the indicator is configured to be selected and held by the user to slide the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, the indicator is further configured to be released by the user after sliding the indicator, wherein releasing the indicator sets the rate to zero. In one example, releasing the indicator holds a present value of the current magnitude constant. In one example, the indicator is slidable to adjust a rate at which the current magnitude is increased and to adjust a rate at which the current magnitude is decreased. In one example, the method further comprises displaying a present value of the current magnitude on the screen. In one example, the implantable stimulator device comprises stimulation circuitry controllable by amplitude values provided by a digital amplitude bus, and wherein the indicator adjusts the rate at which the current magnitude is adjusted by adjusting a rate at which the amplitude values are adjusted. In one example, the method further comprises displaying on the GUI a graph of a relationship that dictates how the current magnitude varies as a function of the amplitude values. In one example, in one example, the method further comprises displaying a present value of the current magnitude on the graph. In one example, the relationship is selectable by the user using the GUI. In one example, a present value of the current magnitude is held constant when the indicator is at a zero position. In one example, the indicator is further configured to be released by the user after sliding the indicator. In one example, the method further comprising reducing a present value of the current magnitude by a set amount when the indicator is released by the user if a present value of the rate equals or is above the rate threshold. In one example, the implantable stimulator device comprises stimulation circuitry controllable by amplitude values provided by a digital amplitude bus, the method further comprising reducing the present value of the current magnitude by the set amount by reducing a present amplitude value by a set amount. In one example, the set amount the present amplitude value is reduced comprises a percentage reduction in the present amplitude value. In one example, the set amount the present amplitude value is reduced comprises a number of amplitude value steps. In one example, the method further comprises holding a present value of the current magnitude when the indicator is released by the user if a present value of the rate is below the rate threshold. In one example, the indicator is linearly slidable by the user. In one example, the indicator is rotationally slidable by the user.

A system is disclosed, which may comprise: an implantable stimulator device comprising a plurality of electrodes configured to provide stimulation to a patient's tissue; and an external device configured to program the implantable stimulator device, the external device comprising: a screen, and control circuitry programmed with software, wherein the software when executed is configured to render a graphical user interface (GUI) on the screen, wherein the GUI includes a slider with an indicator slidable by a user to adjust a rate at which a current magnitude is adjusted at one or more of the electrodes, wherein the rate is a function of a length that the indicator is slid, wherein the control circuitry is configured to provide the current magnitude as adjusted to the implantable stimulator device.

In one example, the indicator comprises an on-screen button configured to be selectable by the user to slide the indicator. In one example, the indicator is configured to be selected and held by the user to slide the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, the indicator is further configured to be released by the user after sliding the indicator, wherein releasing the indicator sets the rate to zero. In one example, releasing the indicator holds a present value of the current magnitude constant. In one example, the indicator is slidable to adjust a rate at which the current magnitude is increased and to adjust a rate at which the current magnitude is decreased. In one example, the GUI further includes an aspect to display a present value of the current magnitude on the screen. In one example, the implantable stimulator device comprises stimulation circuitry controllable by amplitude values provided by a digital amplitude bus, and wherein the indicator adjusts the rate at which the current magnitude is adjusted by adjusting a rate at which the amplitude values are adjusted. In one example, the GUI includes an aspect configured to display a graph of a relationship that dictates how the current magnitude varies as a function of the amplitude values. In one example, the GUI is configured to display a present value of the current magnitude on the graph. In one example, the aspect comprises an option to allow the user to select the relationship. In one example, the slider comprises a zero position, wherein a present value of the current magnitude is held constant when the indicator is at the zero position. In one example, the indicator is further configured to be released by the user after sliding the indicator. In one example, the GUI further comprises a rate threshold, wherein the GUI is configured when the indicator is released by the user to reduce a present value of the current magnitude by a set amount if a present value of the rate equals or is above the rate threshold. In one example, the implantable stimulator device comprises stimulation circuitry controllable by amplitude values provided by a digital amplitude bus, and wherein the GUI is configured to reduce the present value of the current magnitude by the set amount by reducing a present amplitude value by a set amount. In one example, the set amount the present amplitude value is reduced comprises a percentage reduction in the present amplitude value. In one example, the set amount amplitude value is reduced comprises a number of amplitude value steps. In one example, the GUI is further configured when the indicator is released by the user to hold the present value of the current magnitude constant if the present value of the rate is below the rate threshold. In one example, the indicator is linearly slidable by the user. In one example, the indicator is rotationally slidable by the user.

An external device is disclosed which is configured to program an implantable stimulator device having a plurality of electrodes configured to provide stimulation to a patient's tissue. The external device may comprise: a slider controllable by user to adjust a rate at which a current magnitude is adjusted at one or more of the electrodes, wherein the rate is a function of a length that an indicator is slid in the slider; and control circuitry configured to provide the current magnitude as adjusted to the implantable stimulator device.

In one example, the external device further comprises: In one example, a screen, and wherein the control circuitry programmed with software, wherein the software when executed is configured to render a graphical user interface (GUI) on the screen, wherein the GUI comprises the slider and the indicator. In one example, the indicator comprises an on-screen button configured to be selectable by the user to slide the indicator. In one example, the indicator is configured to be selected and held by the user to slide the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, the indicator is further configured to be released by the user after sliding the indicator, wherein releasing the indicator sets the rate to zero. In one example, releasing the indicator holds a present value of the current magnitude constant. In one example, the slider is controllable by user to adjust a rate at which the current magnitude is increased and to adjust a rate at which the current magnitude is decreased. In one example, the implantable stimulator device comprises stimulation circuitry controllable by amplitude values provided by a digital amplitude bus, and wherein the slider adjusts the rate at which the current magnitude is adjusted by adjusting a rate at which the amplitude values are adjusted. In one example, a present value of the current magnitude is held constant when the indicator is at a zero position. In one example, the indicator is further configured to be released by the user after sliding the indicator. In one example, the external device is programmed with a rate threshold, wherein the external device is configured when the indicator is released by the user to reduce a present value of the current magnitude by a set amount if a present value of the rate equals or is above the rate threshold. In one example, the implantable stimulator device comprises stimulation circuitry controllable by amplitude values provided by a digital amplitude bus, and wherein the external device is configured to reduce the present value of the current magnitude by the set amount by reducing the present amplitude value by a set amount. In one example, the set amount the present amplitude value is reduced comprises a percentage reduction in the present amplitude value. In one example, the set amount the present amplitude value is reduced comprises a number of amplitude value steps. In one example, the external device is further configured when the indicator is released by the user to hold the present value of the current magnitude constant if the present value of the rate is below the rate threshold. In one example, the external device comprises a peripheral device, and wherein the slider is on the peripheral device. In one example, the peripheral device is configured to be coupled to a port of the external device.

A computer-readable medium is disclosed having instructions stored thereon, wherein the instructions are configured to be executable in an external device for controlling an implantable stimulator device, wherein the instructions cause control circuitry in the external device to: render on a screen of the external device a graphical user interface (GUI), wherein the GUI includes a slider with an indicator; enable receipt of an input at the GUI from a user to slide the indicator to adjust a rate at which a current magnitude is adjusted at one or more of the electrodes, wherein the rate is a function of a length that the indicator is slid; and provide the current magnitude as adjusted to the implantable stimulator device.

A method is disclosed for controlling an implantable stimulator device using an external device. The method may comprise: providing on a screen of the external device a graphical user interface (GUI), wherein the GUI includes an indicator; receiving at the GUI a first input from a user to control the indicator to adjust a rate at which a current magnitude is increased at one or more of the electrodes; providing the current magnitude as increased to the implantable stimulator device; receiving at the GUI a second input from the user to release the indicator; and reducing a present value of the current magnitude at the implantable stimulator device by a set amount if a present value of the rate equals or is above a rate threshold when the indicator is released.

In one example, the implantable stimulator device comprises stimulation circuitry controllable by amplitude values provided by a digital amplitude bus, and wherein present value of the current magnitude is reduced by the set amount by reducing the present amplitude value by a set amount. In one example, the set amount the present amplitude value is reduced comprises a percentage reduction in the present amplitude value. In one example, the set amount the present amplitude value is reduced comprises a number of amplitude value steps. In one example, reducing the present value of the current magnitude by a set amount does not comprise reducing the present value of the current magnitude to zero. In one example, reducing the present value of the current magnitude by a set amount comprises reducing the present value of the current magnitude to zero. In one example, the method further comprises holding the present value of the current magnitude constant if the present value of the rate is below the rate threshold when the indicator is released. In one example, the indicator is configured to be slidable by the user to adjust the rate at which the current magnitude is increased. In one example, the rate is a function of a length that the indicator is slid. In one example, the indicator is configured to be selected and held by the user to slide the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, the present value of the current magnitude is held constant when the indicator is at a zero position. In one example, releasing the indicator sets the rate to zero. In one example, the method further comprises displaying the present value of the current magnitude on the screen. In one example, the implantable stimulator device comprises stimulation circuitry controllable by amplitude values provided by a digital amplitude bus, and wherein the indicator adjusts the rate at which the current magnitude is increased by adjusting a rate at which the amplitude values are increased. In one example, the method further comprises displaying a graph of a relationship that dictates how the current magnitude varies as a function of the amplitude values. In one example, the method further comprises displaying a present value of the current magnitude on the graph. In one example, the relationship is selectable by the user using the GUI.

A system is disclosed, which may comprise: an implantable stimulator device comprising a plurality of electrodes configured to provide stimulation to a patient's tissue; and an external device configured to program the implantable stimulator device, the external device comprising: a screen, and control circuitry programmed with software, wherein the software when executed is configured to render a graphical user interface (GUI) on the screen, wherein the GUI includes an indicator controllable to adjust a rate at which a current magnitude is increased at one or more of the electrodes when the indicator is selected by a user, wherein the GUI further comprises a rate threshold, wherein the GUI is configured when the indicator is released by the user to reduce a present value of the current magnitude by a set amount if a present value of the rate equals or is above the rate threshold, wherein the control circuitry is configured to provide the current magnitude as adjusted and reduced to the implantable stimulator device.

In one example, the implantable stimulator device comprises stimulation circuitry controllable by amplitude values provided by a digital amplitude bus, and wherein the GUI is configured to reduce the present value of the current magnitude by the set amount by reducing the present amplitude value by a set amount. In one example, the set amount the present amplitude value is reduced comprises a percentage reduction in the present amplitude value. In one example, the set amount the present amplitude value is reduced comprises a number of amplitude value steps. In one example, reducing the present value of the current magnitude by a set amount does not comprise reducing the present value of the current magnitude to zero. In one example, reducing the present value of the current magnitude by a set amount comprises reducing the present value of the current magnitude to zero. In one example, the GUI is further configured when the indicator is released by the user to hold the present value of the current magnitude constant if the present value of the rate is below the rate threshold. In one example, the indicator is configured to be slidable by the user to adjust the rate at which the current magnitude is increased. In one example, the rate is a function of a length that the indicator is slid. In one example, the indicator is configured to be selected and held by the user to slide the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, the GUI comprises a zero position for the indicator, wherein the present value of the current magnitude is held constant when the indicator is at the zero position. In one example, releasing the indicator sets the rate to zero. In one example, the indicator is further controllable to adjust a rate at which the current magnitude is decreased. In one example, the GUI further includes an aspect to display the present value of the current magnitude on the screen. In one example, the implantable stimulator device comprises stimulation circuitry controllable by amplitude values provided by a digital amplitude bus, and wherein the indicator adjusts the rate at which the current magnitude is increased by adjusting a rate at which the amplitude values are increased. In one example, the GUI includes an aspect configured to display a graph of a relationship that dictates how the current magnitude varies as a function of the amplitude values. In one example, the GUI is configured to display a present value of the current magnitude on the graph. In one example, the aspect comprises an option to allow the user to select the relationship.

An external device is disclosed which is configured to program an implantable stimulator device having a plurality of electrodes configured to provide stimulation to a patient's tissue. The external device may comprise: an indicator controllable by user to adjust a rate at which a current magnitude is increased at one or more of the electrodes, wherein the external device is programmed with a rate threshold, wherein the external device is configured when the indicator is released by the user to reduce a present value of the current magnitude by a set amount if a present value of the rate equals or is above the rate threshold; and control circuitry configured to provide the current magnitude as adjusted and reduced to the implantable stimulator device.

In one example, the external device further comprises: a screen, and wherein the control circuitry programmed with software, wherein the software when executed is configured to render a graphical user interface (GUI) on the screen, wherein the GUI comprises the indicator. In one example, the indicator comprises an on-screen button configured to be selectable by the user to control the indicator. In one example, the indicator is configured to be selected and held by the user to control the indicator. In one example, the indicator is configured to be selected and held by the user using a mouse or touch pad associated with the external device. In one example, the screen comprises a touch screen, and wherein the indicator is configured to be selected and held by a finger of the user on the screen. In one example, releasing the indicator sets the rate to zero. In one example, the external device is configured when the indicator is released by the user to hold the present value of the current magnitude constant if the present value of the rate is below the rate threshold. In one example, the implantable stimulator device comprises stimulation circuitry controllable by amplitude values provided by a digital amplitude bus, and wherein the indicator adjusts the rate at which the current magnitude is increased by adjusting a rate at which the amplitude values are increased. In one example, the set amount the present amplitude value is reduced comprises a percentage reduction in the present amplitude value. In one example, the set amount the present amplitude value is reduced comprises a number of amplitude value steps. In one example, the present value of the current magnitude is held constant when the indicator is at a zero position. In one example, the indicator is slidable by the user to adjust the rate at which a current magnitude is increased. In one example, the rate is a function of a length that the indicator is slid. In one example, the external device comprises a peripheral device, and wherein the indicator is on the peripheral device. In one example, the peripheral device is configured to be coupled to a port of the external device.

A computer-readable medium is disclosed having instructions stored thereon, wherein the instructions are configured to be executable in an external device for controlling an implantable stimulator device, wherein the instructions cause control circuitry in the external device to: render on a screen of the external device a graphical user interface (GUI), wherein the GUI includes an indicator; enable receipt of a first input at the GUI from a user to control the indicator to adjust a rate at which a current magnitude is increased at one or more of the electrodes; provide the current magnitude as increased to the implantable stimulator device; enable receipt of a second input at the GUI from the user to release the indicator; and reduce a present value of the current magnitude at the implantable stimulator device by a set amount if a present value of the rate equals or is above a rate threshold when the indicator is released.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

FIGS. 5A and 5B show different external devices that can be used to program the IPG.

FIGS. 7A and 7B show how the amplitude slider can be used to quickly ramp the current to a target magnitude value.

FIGS. 8A and 8B show how the amplitude slider can also be decreased when establishing the current to a target magnitude value.

FIGS. 9A and 9B show use of a drop back feature in the GUI which is used to reduce the amplitude by a pre-determined amount under certain conditions when the amplitude slider is released.

FIGS. 10A to 10C shows different ways in which amplitude slider functionality can be implemented.

FIG. 11A shows how the GUI can be used to select a relationship that determines how the current magnitude varies with amplitude, while FIGS. 11B and 11C show an example of DAC circuitry that is programmable in accordance with the selected relationship.

FIG. 12A shows use of the GUI to program the DAC circuitry with an exponential relationship, while

DETAILED DESCRIPTION

Figure 3A:
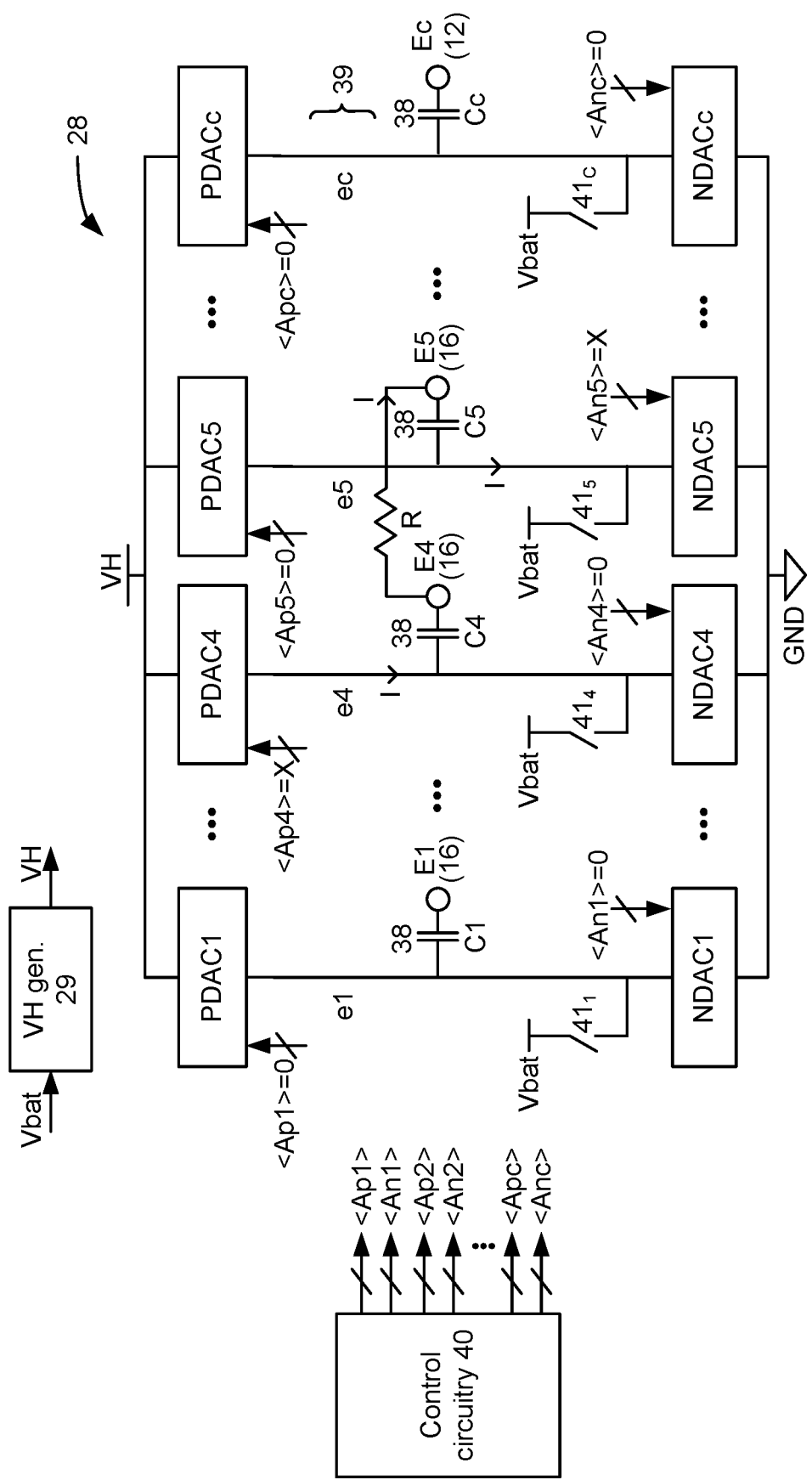
FIGS. 3A and 3B show different examples of stimulation circuitry, including PDACs and NDACs, useable in the IPG, in accordance with the prior art.
Figure 3B:
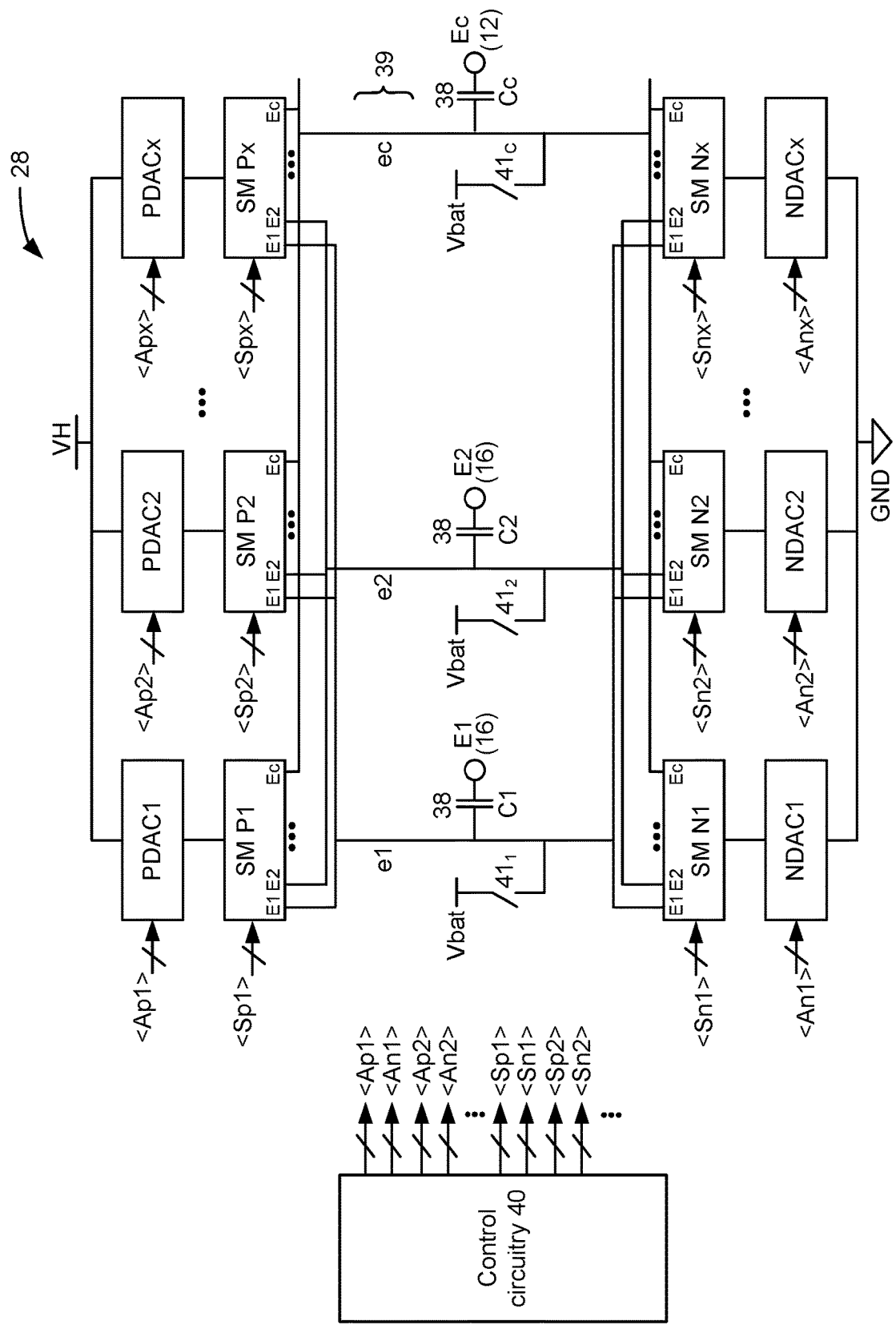
Figure 4:
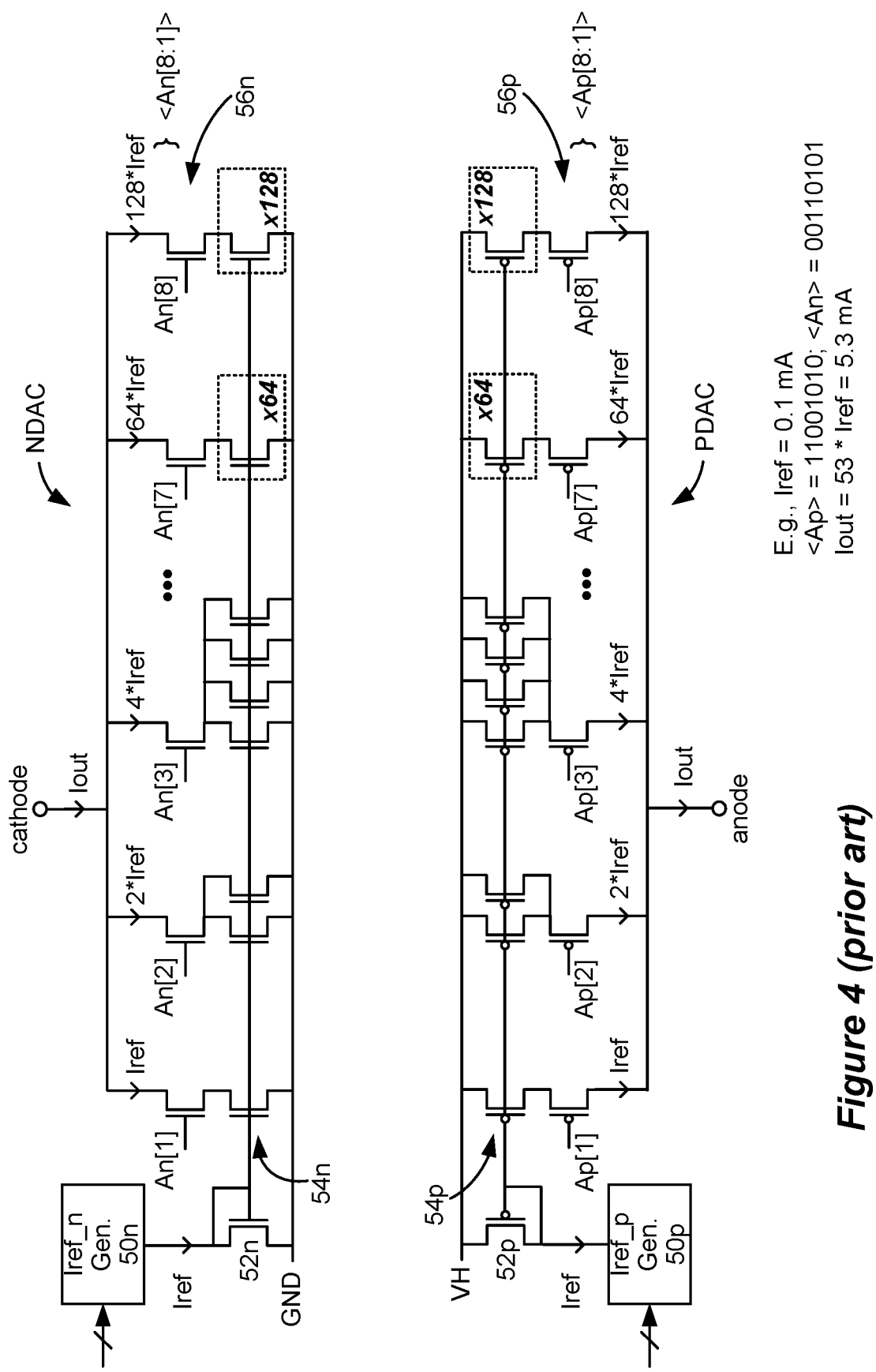
FIG. 4 shows circuit details of a PDAC and NDAC useable in the stimulation circuitries of FIGS. 3A and 3B, in accordance with the prior art.
Figure 5B:
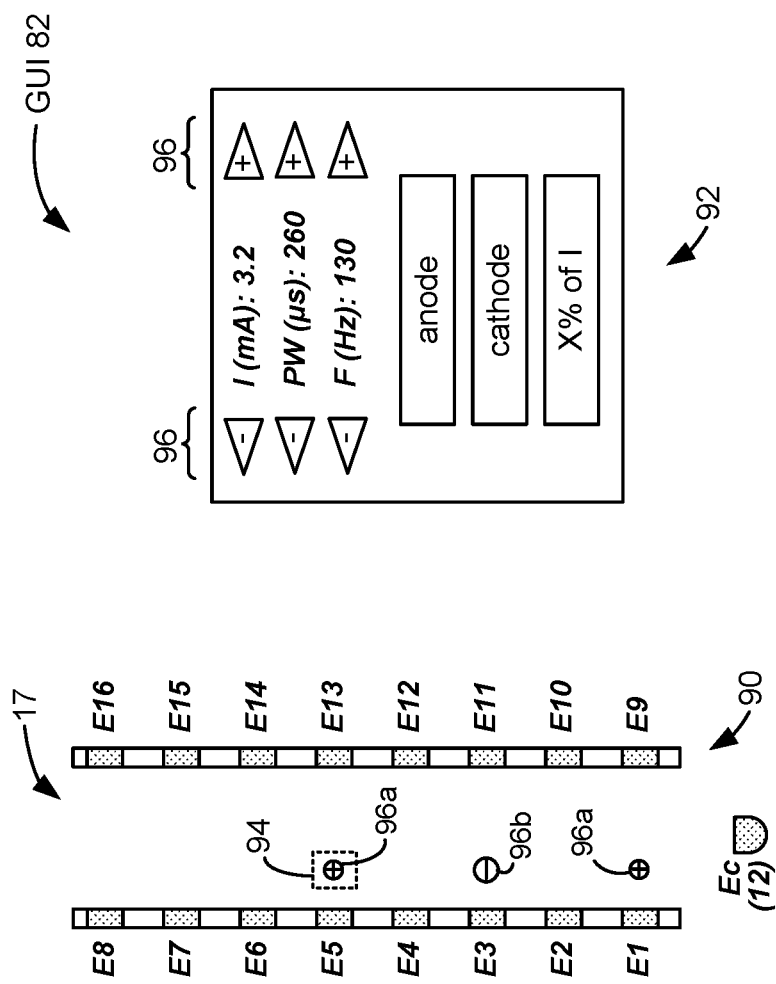

The inventor sees room for improvement in the Graphical User Interfaces (GUIs) that are used in external devices to control to the IPG's programming. Whether one considers the GUI as rendered on the patient remote control 60 or the clinician programmer 70 (FIGS. 5A and 5B), the ability to adjust the magnitude of the stimulation at prescribed electrodes (e.g., the magnitude of the current) is typically done incrementally. Such incremental adjustment tends to be dependent on the type of stimulation circuitry 28 (FIGS. 3A, 3B, and 4) used. Consider for example use of the DAC circuitry (PDAC and NDAC) of FIG. 4. As noted earlier, the magnitude of the current provided by such circuitry is controllable via digital amplitude buses (<Ap> and <An>). As the amplitude value A on these buses is incremented (under control of the external device), the magnitude of the current output also increments (e.g., by Iref=0.1 mA).

Consistent with such DAC circuitry, the GUI of the external device allows the user to increment (or decrement) the amplitude values, which increments (or decrements) the magnitude of the current in steps of 0.1 mA. Often, the current magnitude is incremented starting at zero. This can be preferred for safety reasons: when determining a current magnitude that is appropriate for the patient (e.g., during a fitting session), the sensitivity of the patient's neural tissue to current may not be known, and therefore it can be advisable to start the magnitude of the current at zero and increment it upwards to ensure that the patient is not discomforted by a sudden large increase in the magnitude. Incrementing the current can be a slow and laborious process, particularly when starting from zero. Assume for example that a particular patient would be benefitted by receiving a current magnitude of +10 mA. When starting from zero, and assuming that the GUI 82 of the clinician programmer 70 is used (FIG. 5B), the clinician would move the mouse cursor 94 to on-screen buttons 96, and would "click" (e.g., using the left mouse button) to increase the current magnitude. A first click would set Iout to 0.1 mA, which would be affected by transmitting an amplitude value Ap=1 to the IPG (along with other stimulation parameters such as pulse width and frequency). A second click would set Iout to 0.2 mA (Ap=2), and so on. Notice that the user would have to click the magnitude increase button 100 times to eventually adjust the current to the desired value of Iout=10 mA. This is slow and inconvenient for both clinician and patient. The same is true when the patient adjusts the current magnitude using the GUI of his remote control 60. In this circumstance, the patient would typically use buttons 65 on the device associated with the GUI to incrementally increase the current (FIG. 5A), and again would have to press such buttons a large number of times.

Figure 6:
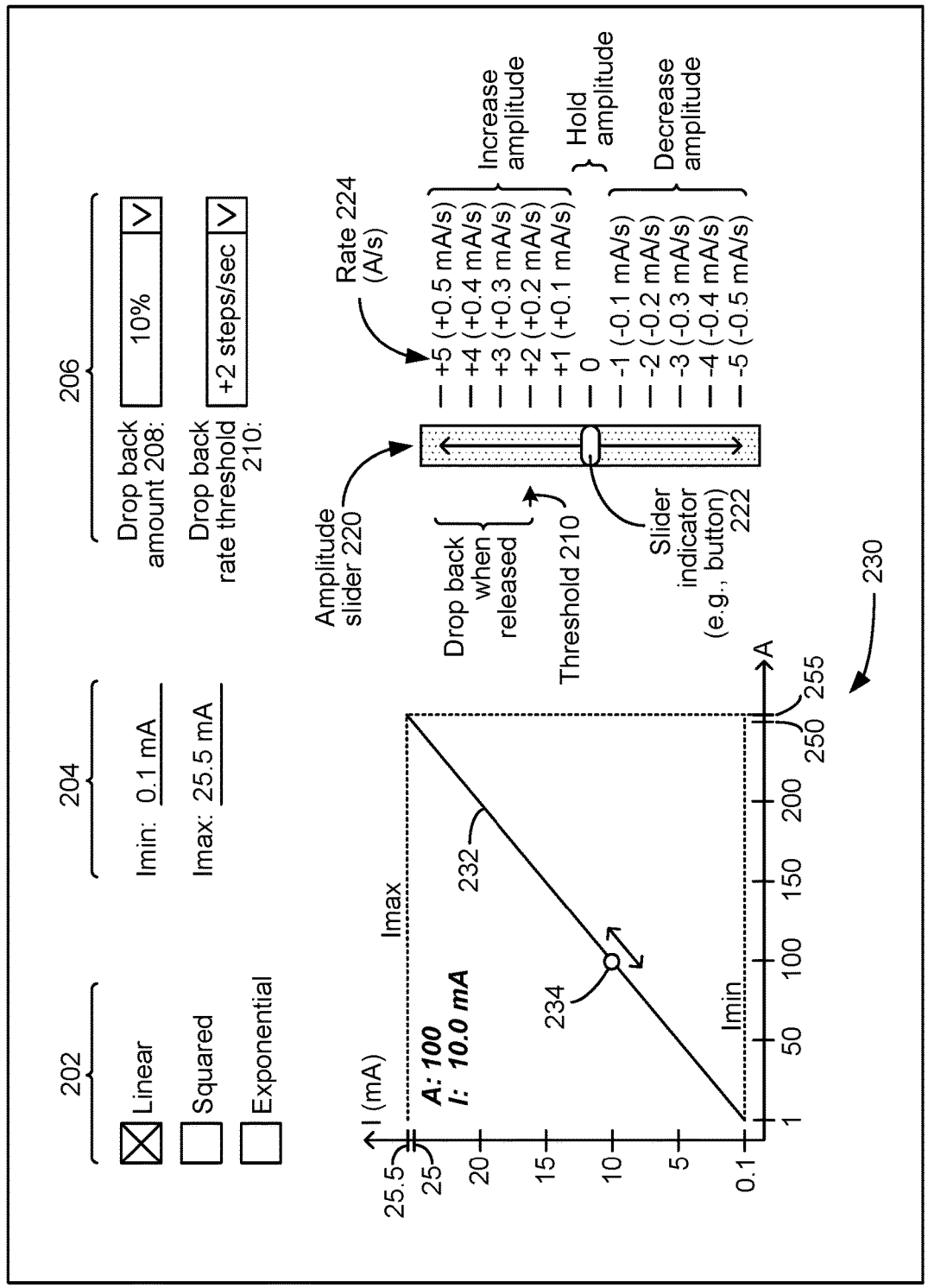
FIG. 6 shows an example of an improved Graphical User Interface that may be used with an external device to control programming of the IPG, which includes an amplitude slider as well as other control elements.

To address these problems, the inventor has developed an improved GUI 200 for use with an IPG's external devices, as shown first in FIG. 6. The GUI 200 is shown as implemented on a clinical programmer 70, i.e., as rendered on its screen 74, and shows improved aspects that can be used to adjust the magnitude of the stimulation. In an actual implementation, the GUI 200 would likely include aspects to adjust other stimulation parameters as well, such as frequency and pulse width, and to select electrodes within the electrode array 17 for use, as shown earlier in FIG. 5B. However, such other aspects are not shown in FIG. 6 for simplicity, which instead only focuses on magnitude (amplitude) adjustment. While shown in the context of a clinician's programmer 70, the GUI aspects shown in FIG. 6 could also be used in the GUI of a patient's remote control device 60 as well, or in any other external device that is useable to control operation of the IPG 10. In this regard, the GUI 200 could include other buttons which may be present on the external device (e.g., 65, FIG. 5A), which buttons may be separate from the devices' screen. Note that GUI 200 could comprise an improvement or addition to a GUI 82 (FIG. 5B) already present in an external device, and may be built and stored similarly as software 84 operating within the external device.

Not all aspects of GUI 200 as shown in FIG. 6 are necessary in an actual implementation, and some aspects may be specific to use with IPG's having particular DAC circuitry designs, as discussed in further detail later with respect to FIGS. 10A to 11B. FIG. 6 assumes that the DAC circuitry in the IPG 10 is designed as described earlier in FIGS. 3A-4. As such, the current magnitude providable by the DAC circuitry, and thus programmable at the GUI 200, can be set from 0 to 25.5 mA in 0.1 mA increments, using amplitude values A from 0 to 255. (From this point forward, amplitude values are described using variable A, which may comprise either a source current amplitude value Ap useable to control a PDAC or a sink current amplitude value An useable to control an NDAC).

The GUI 200 in FIG. 6 includes means to display the currently-selected current magnitude to the user, shown generally at 230. The currently-selected current magnitude (I=10 mA) may be displayed textually to the user, as may the corresponding amplitude value (A=100) used by the DAC circuitry to provide that current. The relationship 232 between the current magnitude I and the amplitude values A may be graphed in the GUI 200 as shown, and in this example this relationship is linear (I=0.1 mA*A). A point 234 on this relationship 232 can also indicate the currently-selected current magnitude. Note that it may not be necessary to display the amplitude value A to the user, although this is shown in FIG. 6 and subsequent figures as it useful to illustrating aspects of the disclosed techniques.

The current magnitude is controllable in GUI 200 using an amplitude slider 220, which may be rendered on the screen 74. The slider 220 includes an on-screen indicator 222 which a user can slide (vertically as shown) along the length of the slider. Manners in which the indicator can be controlled are discussed further below. The slider 220 is used to control the rate 224 at which the current is increased or decreased, and in the example shown such rate is defined with respect to the amplitude values A used to control the DAC circuitry. This rate 224—e.g., the number of amplitude increments per second (A/s)—is preferably indicated next to the slider 220 as shown (e.g., +5=five amplitude values per second). This rate may also be expressed and indicated as a rate at which the current magnitude will change (e.g., +5=+0.5 mA/s), which may be more meaningful to the user. At rest, i.e., when the current is not being adjusted or is being held constant, the slider's indicator 222 is positioned as shown in FIG. 6 at the zero position.

If it is desirable to increase the current, the user may slide the indicator 222 upwards from the zero position, with a larger slide length increasing the amplitude at a larger rate. For example, if the user slides the indicator 222 a small length to a rate of +1, the amplitude will increase from its current setting (e.g., A=100, I=10 mA) at a rate of one amplitude value per second. Thus, after one second, the amplitude value will be incremented by one (A=101), which will program the IPG 10 to increase the current to 10.1 mA. After another second in this position (two seconds in total), the amplitude value will again be incremented by one (A=102), which will increase the current to 10.2 mA, etc. In short, when the slider's indicator 222 is held at rate +1, the current provided by the IPG 10 (at selected electrode(s)) will increase at a rate of 0.1 mA/s, with the amplitude values being incremented every second.

If the user slides the indicator 222 a larger length to a rate of +2, the amplitude will increase from its current setting (e.g., A=100, I=10 mA) at a rate of two amplitude values per second. This may cause the amplitude value to be incremented more quickly. Thus, after 0.5 seconds in this position, the amplitude value will be incremented by one (A=101), which will program the IPG 10 to increase the current to 10.1 mA. After another 0.5 seconds in this position (one second in total), the amplitude value will again be incremented by one (A=102), which will increase the current to 10.2 mA. In short, when the slider's indicator 222 is held at rate +2, the current provided by the IPG 10 will increase at a rate of 0.2 mA/s. Note that the rate at which the amplitude value is incremented could vary. For example, instead of incrementing the amplitude value by one every 0.5 seconds, the GUI 200 could be programmed to increment the amplitude value by two every second (which keeps the same rate).

If the user slides the indicator 222 to a rate of +5, the amplitude will increase from its current setting (e.g., A=100, I=10 mA) at a rate of five amplitude values per second. Thus, after 0.2 seconds in this position, the amplitude value will be incremented by one (A=101), which will program the IPG 10 to increase the current to 10.1 mA. After another 0.2 seconds in this position (0.4 seconds total), the amplitude value will again be incremented by one (A=102), which will increase the current to 10.2 mA. In short, when the slider's indicator 222 is held at rate +5, the current provided by the IPG 10 will increase at a rate of 0.5 mA/s. Again, the rate at which the amplitude values is incremented could vary, with the GUI 200 incrementing the amplitude value by one every 0.2 seconds, or incrementing the amplitude value by five every second.

If it is desirable to decrease the current, the user may slide the indicator 222 downwards from the zero position. For example, if the user slides the indicator 222 to a rate of −1, the amplitude will decrease from its current setting (e.g., A=100, I=10 mA) at a rate of one amplitude value per second. After one second in this position, the amplitude value will be decremented by one (A=99), which will program the IPG 10 to decrease the current to 9.9 mA. After another second in this position (two seconds in total), the amplitude value will again be decremented by one (A=98), which will decrease the current to 9.8 mA, etc. Similar to what was described above, sliding the indicator 222 to different negative rates 224 will decrease the current at different rates, which can cause the GUI 200 to decrement the amplitude values at different rates.

Figure 7A:
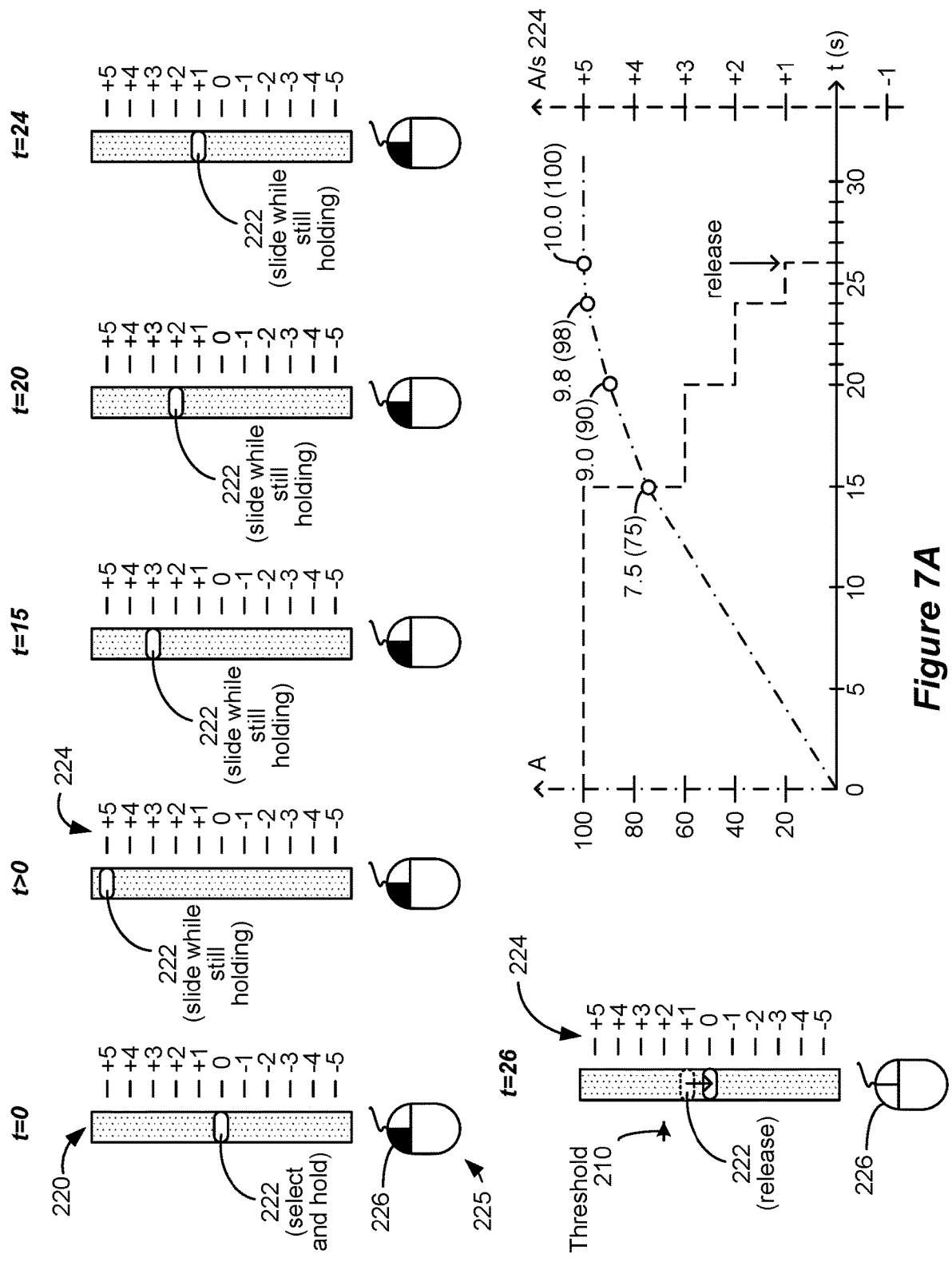

FIGS. 7A and 7B show an example in which the amplitude slider 220 of GUI 200 is used to adjust the current magnitude of a patient's IPG 10 starting from zero, and further describe manners in which indicator 222 can controlled. In particular, these figures show that the indicator 222 can comprise an on-screen button that a user can select, hold, and "release" at different points in time. In one example, this can occur using a mouse 225 associated with the clinician's programmer 70. The indicator 222 can be selected using mouse 225, i.e., by moving cursor 94 (FIG. 5B) to the indicator 222 and clicking it using the mouse's left button 226 for example. Once selected, the left mouse button 226 can continue to be depressed to "hold" the indicator 222 to allow it be to slid to different rates along the slider 220. The depressed left mouse button 226 can later be released (unheld), as explained further below.

In the example shown in FIGS. 7A and 7B, it is assumed (although not necessarily known at the outset), that a patient would therapeutically benefit from a current magnitude equal to 10.0 mA. At time t=0 seconds, it is assumed that the clinician has selected and held indicator 222, and has essentially immediately thereafter (t>0) slid (while still holding) the indicator 222 to an amplitude rate (224) of +5. As explained above, this would increase the amplitude value A at a rate of 5 steps/s, which would in this example increase the current magnitude I at a rate of 0.5 mA/sec. Notice then that the current magnitude and amplitude value in this example, although starting at zero for safety reasons, are initially increased quickly, and without the clinician needing to repeatedly click a button each time the current and amplitude are incrementally increased. As the user continues to hold the indicator 222, the current magnitude and amplitude value continue to increase at the prescribed rate. Notice that while the current magnitude and amplitude values increase relatively quickly and conveniently, they preferably also increase slowly enough to allow the clinician to monitor and received feedback from the patient, and to stop increasing the current—for example, by releasing the indicator 222—should the patient experience discomfort. Other aspects of GUI 200 that can be used to mitigate the potential for patient discomfort are discussed further below.

At time t=15 seconds, the current magnitude I has increased to 7.5 mA, and the amplitude value A has increased to 75. At this point, it is assumed that the clinician slid (while still holding) the indicator 222 in the slider 220 to +3, which will slow down the rate at which current magnitude and amplitude value will increase (i.e., A now increases at 3 steps/s, while I increases at 0.3 mA/s). This reduction in the rate has possibly occurred because the patient has provided feedback concerning the extent to which the increasing current is affecting his symptoms, or simply because the clinician may realize that the current magnitude is now relatively high, and thus that the rate of increase should slow. At time t=20 seconds, the current magnitude I has increased to 9.0 mA, and the amplitude value A has increased to 90, and the clinician has slid (while still holding) the indicator 222 in the slider 220 to +2, to further reduce the rate at which the current magnitude and amplitude values increase (to 2 steps/s and 0.2 mA/s respectively). At time t=24 seconds, the current magnitude I has increased to 9.8 mA, and the amplitude value A has increased to 98, and the clinician has slid (while still holding) the indicator 222 in the slider 220 to +1, to still further reduce the rate at which the current magnitude and amplitude values increase (to 1 step/s and 0.1 mA/s respectively). One might assume at the point that the patient is starting to indicate therapeutic effectiveness to the clinician.

At time t=26 seconds, the current magnitude I has increased to 10.0 mA (the target value in this example), and the amplitude value A has increased to 100. At this point, and again perhaps in response to feedback from the patient, the clinician releases the indicator 222 that has been held up to this point. For example, the clinician may at this point stop depressing the left mouse button 226. The indicator 222, once released, returns in the slider 220 to a rate (224) of zero. As such, the currently-established current magnitude and amplitude values are held constant, and are no longer increased (or decreased). FIG. 7B shows how the point 234 indicating the current magnitude has moved with reference to relationship 232 as a function of time, which provides useful feedback to the clinician. At this point, although not shown, the indicator 222 in the slider 220 could again be selected and held to increase or decrease the current magnitude from its currently-established value, as might be necessary to fine tune the current magnitude that is optimal for the patient. (It might be expected that such fine tuning would occur at low rates 224, such as +1 or −1). Using the slider to decrease the current is explained below with reference to FIGS. 8A and 8B. To summarize, using GUI 200, the clinician has been able to quickly establish an appropriate current magnitude for the patient, starting from zero. The rate of increase (or decrease) can be easily established by the clinician by sliding and holding the indicator 222. This rate conveniently may be high initially, but then reduced as target values of current magnitude are approached. Significantly, the clinician has not needed to select (click) a button in the GUI 200 for each and every change in current magnitude (amplitude value) that is required.

Figure 8A:
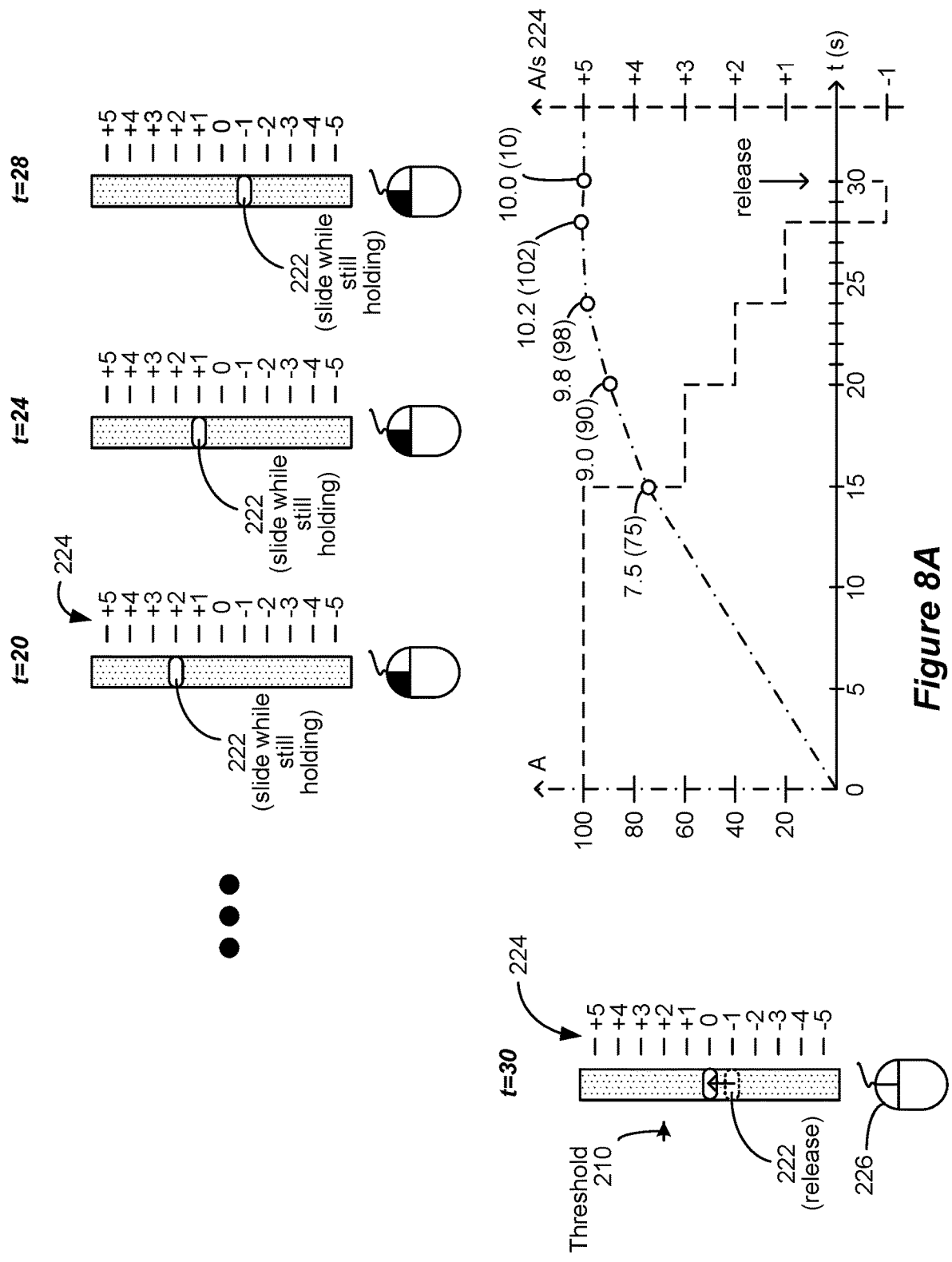

As just mentioned, the amplitude slider 220 can also be used to decrease the current magnitude at desired rates, and FIGS. 8A and 8B show this example. This example begins as in FIG. 7A, with the indicator 222 slid and held to a high rate of increase (+5). At time t=15 seconds, when the amplitude value is at 75 (I=7.5 mA), the rate of increase is reduced but is still relatively high (+3). At time t=20 seconds, when the amplitude value is at 90 (I=9.0 mA), the rate of increase is further reduced (+2). At time t=24 seconds, when the amplitude value is at 98 (I=9.8 mA), the rate of increase is reduced still further (+1). At time t=28 seconds, the amplitude value is at 102 (I=10.2 mA), which exceeds the assumed target (A=100, I=10.0 mA). It might be assumed at this point that the patient is experiencing discomfort. In response, the clinician (or patient) can slide (while still holding) the indicator 222 to a negative rate (−1), meaning that the current will decrease at a rate of −1 amplitude step per second (or −0.1 mA/s). Were the patient experiencing more significant discomfort, a faster rate of decrease (−2, −3, etc.) could be selected to reduce the current more quickly, although this is not illustrated. At time t=30 seconds, the target is reached (A=100, I=10.0 mA), and the indicator 222 is released (e.g., unheld). This returns the rate to zero, which holds the currently-established current magnitude and amplitude values constant. FIG. 8B shows how the point 234 indicating the current magnitude has moved with reference to relationship 232 as a function of time. In short, the slider 220's rate can be adjusted around the zero rate value to small positive and small negative rates to fine tune the current magnitude to a desired current magnitude appropriate for the patient.

Although the GUI 200 is able to increase the current magnitude at a high rate as just discussed, this raises the concern that the current may be increased too quickly, which may cause the patient discomfort or other problematic symptoms. To mitigate this possibility, the GUI 200 preferably includes drop back functionality, which will under certain circumstances automatically reduce the current magnitude by a prescribed amount when the slider 220's indicator 222 is released. A drop back interface 206 is shown in FIG. 6, and allows the user options to prescribe how drop back functionality will occur.

Option 208 allows the user to prescribe the amount by which the current will be reduced when drop back functionality is engaged. In the example shown in FIG. 6, the current when dropped back will be reduced by 10%, and this preferably occurs by reducing the amplitude value by 10%, as will be explained shortly. However, option 208 can also reduce the current in other manners. For example, option 208 may prescribe that the current will be reduced by a set amount, such as a set number of amplitude value steps (e.g., 20 steps). Option 208 may also allow the user to prescribe current reductions in manners other than amplitude values. For example, option 208 may allow the user to specify a specific reduction in the current magnitude such as a 1 mA reduction, or a reduction of 10%. If option 208 defines the reduction in terms of current magnitude, note that relationship 232 allows such current magnitude reductions to be converted to amplitude values, thus allowing the IPG's DAC circuitry to be properly controlled. (This distinction is more relevant when the relationship 232 between current magnitude and amplitude values is non-linear, as described later with reference to FIGS. 11A-12B). In another example not shown, option 208 may also allow the user to prescribe that the current will be turned off, i.e., set to zero, when drop back functionality is engaged, instead of merely being reduced.

Option 210 allows the user to prescribe the circumstances under which drop back functionality will be engaged. In the example shown, drop back functionality is engaged with reference to a rate threshold 210, which relates to the rate 224 of increase of the slider 220. In the example shown, the drop back threshold rate is set to two steps per second, meaning that if the rate (224) of increase is +2 or higher, then drop back functionality will be engaged to reduce the current (per option 208) when the indicator 222 is released. By contrast, if the rate of increase is lower than +2 (or if the rate is decreasing), drop back functionality will not be engaged when the indicator 222 is released, and instead the current magnitude and amplitude values will be held at their current values. As shown, the threshold 210 once set may be indicated next to the slider 220 to allow the user to see when release of the indicator 222 will and will not engage drop back functionality.

FIG. 7A, described earlier, shows an example in which drop back functionality is not engaged to reduce the current. As discussed in that example, the indicator 222 was released at a time t=26 when the rate was increasing slowly at (+1 A/s). Because this rate is below the drop back rate threshold 210 (+2), the current is not reduced when the indicator 222 is released, and instead the current magnitude and corresponding amplitude value are held at their current values (I=10.0 mA, A=100). In this example, because the slider 220 is set to a low rate of increase (less than threshold 210) when the indicator 222 is released, it is not necessary to engage drop back functionality to reduce the current. Even if the patient is experiencing discomfort, such discomfort should be occurring gradually enough that the clinician (or patient if GUI 200 is used on the patient remote control 60) should instead be able to simply slide the indicator 222 down to reduce the current and the patient's discomfort (as occurred in FIGS. 8A and 8B). Thus, instead of dropping back the current, the current magnitude is held to what is assumed an appropriate magnitude for the patient. Note that FIG. 8A also shows an example in which drop back functionality is not engaged. As discussed in that example, the indicator 222 was released at a time t=30 when the rate was decreasing slowly at (−1 A/s). Because any negative rate would be below a positive drop back rate threshold 210 (+2), the current is not reduced when the indicator 222 is released, and again the current magnitude and corresponding amplitude value are held at their current values (I=10.0 mA, A=100).

Figure 9A:
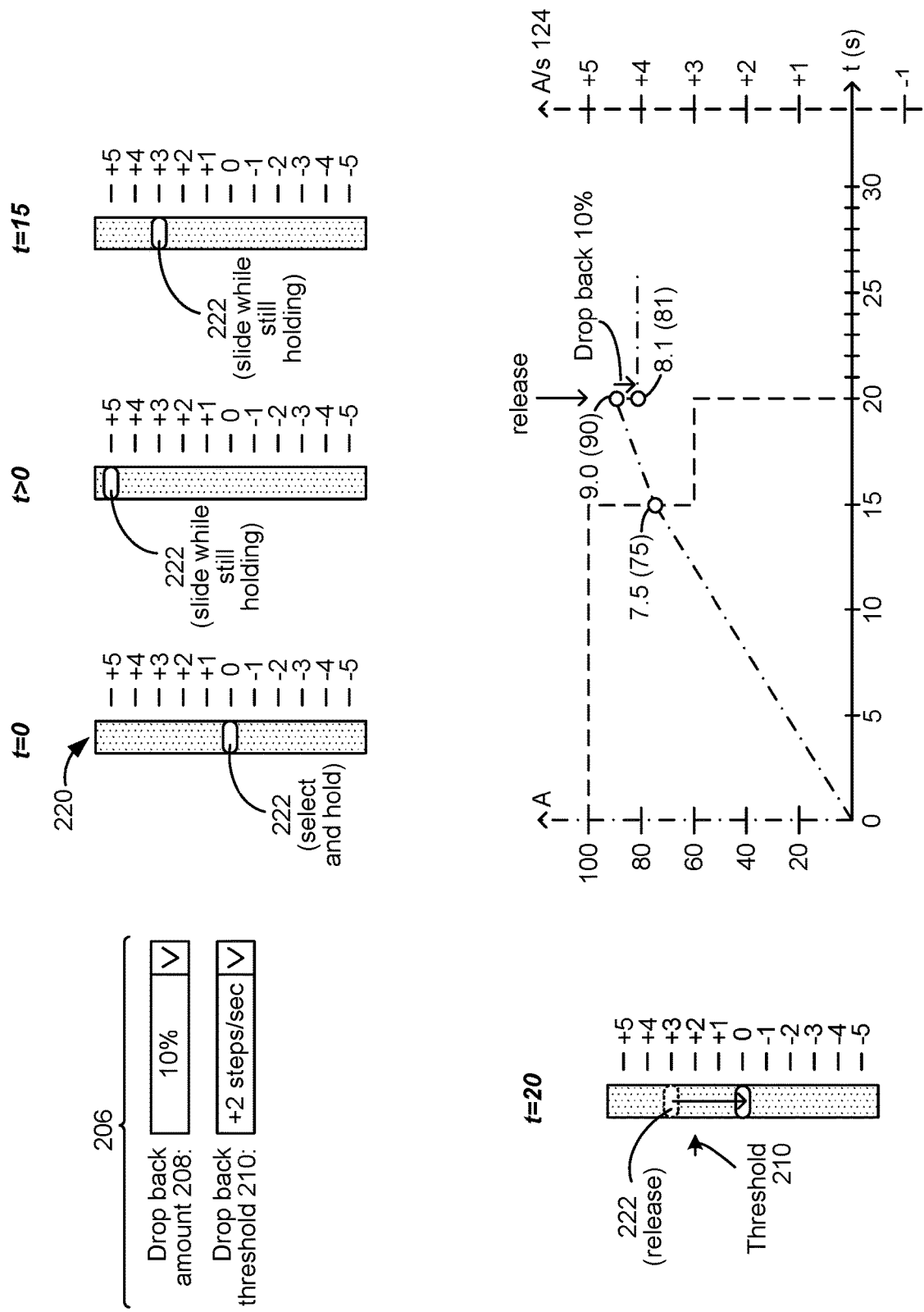

FIG. 9A, by contrast, shows an example in which drop back functionality is engaged to reduce the current. This example begins as in FIG. 7A, with the current magnitude increased at a high rate (+5) from t=0 to 15 seconds. At this point, the rate is dropped but is still relatively high (+3). At time t=20 second, when the amplitude value is at 90 (I=9.0 mA), it might be assumed that the patient is experiencing discomfort. In response, the clinician (or patient) can release the indicator 222, which returns the rate to 0. Further, because the rate 224 at release (+3) is larger than the threshold 210 (+2), drop back functionality is engaged by the GUI 200 to reduce the current in accordance with the prescribed drop back amount 208. In this example, amount 208 is set at 10%, and so the amplitude value, instead of being held constant as in earlier examples, is immediately dropped from 90 to 81, which reduces the current magnitude to 8.1 mA. See also FIG. 9B, showing the drop back in the context of relationship 232. Here, the rationale for engaging the drop back functionality is that it may reasonably be assumed, when the rate of increase is high and the indicator 222 is released, that the patient is experiencing a problem, perhaps because the rate was increasing too quickly causing the current to be higher than what is comfortable level for the patient. To rectify this, and provide immediate relief to the patient, the current is automatically reduced by the drop back amount 208. Thereafter, the clinician can continue to use the slider 220 to adjust the current magnitude, presumably using lower rates of increase or decrease to fine tune the current. As mentioned earlier, and as sometimes might be desired for safety, the drop back amount 208 can also be set to completely shut off the current (A=0) when the indicator 222 is released as well.

Although not shown in FIG. 6, note that the drop back amount 208 may not be constant and instead may be made variable, and in particular may vary as a function of the currently-established rate 224. For example, the GUI 200 may allow the user to prescribe larger drop back amounts 208 when the rate 224 is increase is high, and lower drop back amounts when the rate is low. For example, the drop back amount might be set to 10% when the rate is +5, 7% when the rate is +4, 4% when the rate is +3, etc. The drop back amount 208 may also be dependent on factors other than rate. For example, the drop back amount 208 may vary as a function of the present current magnitude or amplitude value, with higher drop back amounts being used when the current magnitude or amplitude value is higher, and lower amounts when they are lower.

Amplitude rate adjustment can be implemented in other manners, and FIGS. 10A-10C show different examples implemented assuming use of the clinician programmer 70 as the relevant external device. Although not shown, the patent remote controller 60 could also be varied in these respects.

FIG. 10A shows that the amplitude slider 220 need not be of linear shape, and thus that the indicator 222 need not move linearly within the slider. In this example, the slider 220 is circular, and thus the indicators 222 is slid rotationality within the slider. As before, the rate at which the current will increase or decrease is a function of the length that the indicator 222 is slid within the slider 220, with larger clockwise slide lengths increasing the rate of increase, and larger counter-clockwise slide lengths increasing the rate of decrease.

In examples where the indicator 222 comprises a selectable on-screen button, other computer peripherals can be used to select (via cursor 94), hold, slide and release the indicator 222. For example, and as shown in FIG. 10B, a touch pad 240 associated with the clinician programmer's keyboard (not shown) and its buttons could be used. If the clinician programmer 70's screen 74 (FIG. 5A) comprises a touch screen, the indicator 222 can be selected, held, moved, and released on screen using a finger.

The indicator 222 in other examples need not comprise a selectable on-screen button, but instead can merely indicate a rate that is selected and controlled by different means. For example, indicator 222 can be controlled by one or more control devices associated with the external device's user interface. For example, FIG. 10C shows that a physical slider 242 can be used, having a button 244 that can be slid to adjust the rate. This button 244 may also be depressable and releasable, or another button (not shown) may provide this functionality. The adjusted rate selected by the slider 242 can be indicated within the GUI-rendered slider 220 by adjusting the position of the indicator 222 within the slider, thus providing visual feedback in the GUI as to the rate that has been set. Similarly, a joystick 246, or other keys or buttons (e.g., the keys associated with the clinician programmer's computer 70; not shown) can be used to adjust the rate as well. Still further, a rotational button 250 can be included on a peripheral device 248 to adjust the rate, with for example clockwise rotation increasing the rate, and counter-clockwise rotation decreasing the rate (similar to what was shown in FIG. 10A). It is not strictly necessary that the GUI 200 render a slider 220 with an indicator 222 to indicate the selected rate to the user, but again this is preferred for visual feedback. In this regard, note that indicator 222 can comprise the buttons (e.g., 244, 246, 250) associated with the peripheral device. In other examples, the GUI 200 may only indicate (textually or graphically) the current magnitude I (and also possibly the corresponding amplitude value A). Still other means of adjusting the rate, and indicating the selected rate to the user, are possible.

Figure 11A:
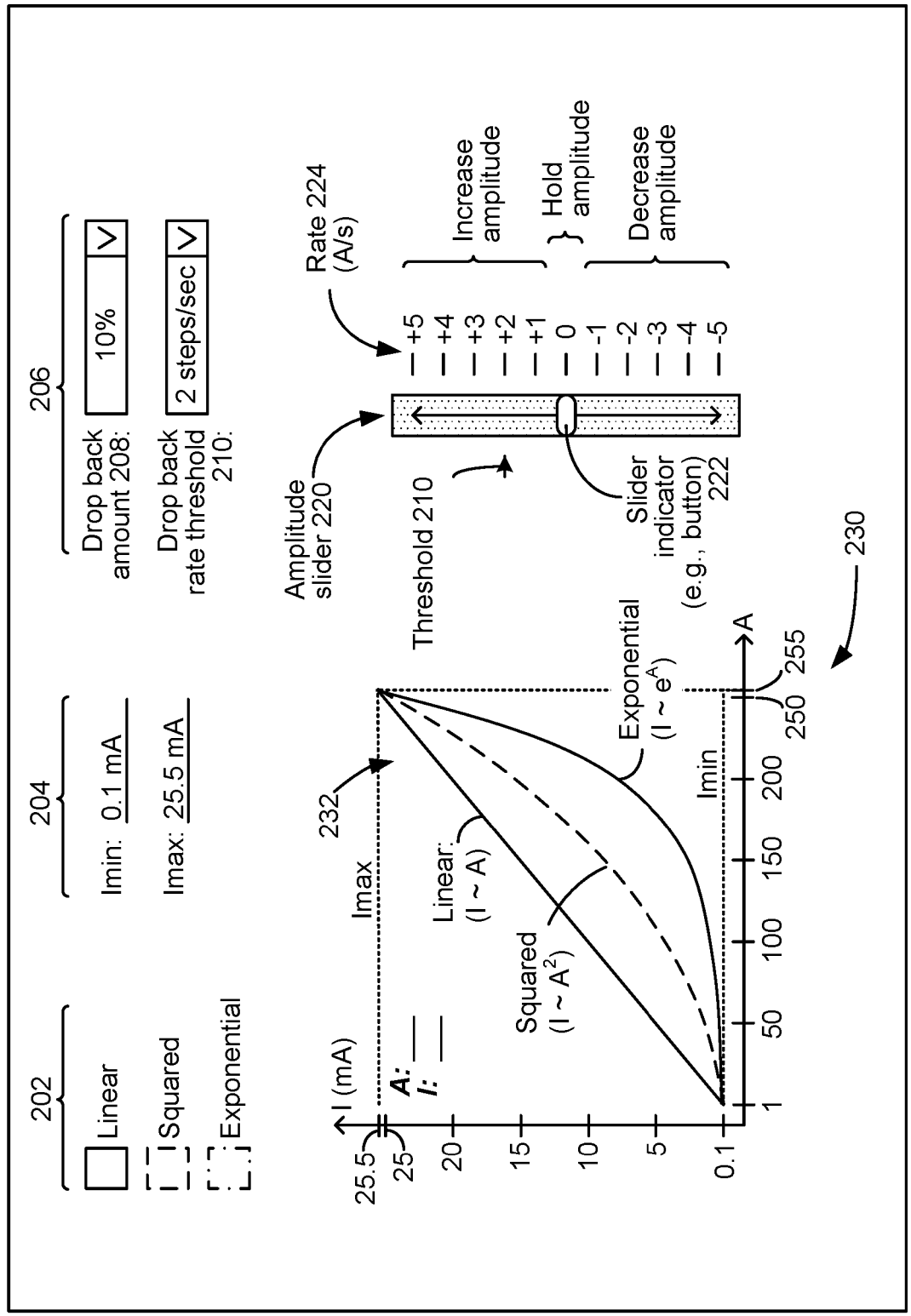

GUI 200 is adaptable to use with IPGs having other DAC circuitry designs, and further may be used to program operation of the DAC circuitry. For example, GUI 200 in FIG. 11A includes an aspect 202 to select how the DAC circuitry will adjust the current magnitude I as a function of amplitude value A. In the example shown, the current magnitude can be programmed to vary linearly with the amplitude value (I~A) (as has been assumed to this point), in a squared relationship with the amplitude value (I~$A^2$), or exponentially with the amplitude value (I~$e^A$). Each of these different relationships 232 are shown in FIG. 11A. GUI 200 further includes an aspect 204 to allow a user to specify maximum (Imax) and minimum (Imin) current magnitudes that the DAC will produce.

Examples of IPG DAC circuitry that are programmable to produce current magnitudes in accordance with selections made at aspects 202 and 204 are disclosed in a U.S. Patent Application Publication 2021/0275798, and entitled "Digital-to-Analog Converter Circuitry for a Stimulator Device Having Non-Linear Amplitude Adjustment," which is incorporated herein by reference in its entirety. An example of this DAC circuitry is only briefly explained here, and is shown in FIGS. 11B and 11C. FIGS. 11B and 11C show an NDAC circuitry design, but as the '798 Publication explains, alterations to the circuitry can be made to form a PDAC as well.

The NDAC circuitry 100 receives a digital amplitude bus <A>, which comprises the amplitude values A provided by the GUI 200. The NDAC circuitry 100 produces an analog output current, I, which is a function of the prescribed amplitude, A, carried by the bus. Depending on the selection made at aspect 202, this output current I varies linearly, squaredly (parabolically), or exponentially as the amplitude values A are incremented, as shown in FIG. 10A.

The NDAC 100 as shown in FIG. 11B includes an input stage 101 and an output stage 104. The input stage in this example includes two biasing stages 102a and 102b. These biasing stages 102a/b can be similar in design, and are used to set the maximum (Imax) and minimum (Imin) values for the current that will be produced at the output, Iout, in accordance with selections made at aspect 204. Each biasing stage 102a/b includes a current source 106a/b which is programmable to produce Imax/Imin as received from the GUI 200.

The maximum and minimum currents Imax and Imin are in this example provided to current-voltage (I-V) selection blocks 108a and 108b (generally 108i), which is shown in further detail in FIG. 11C. I-V selection block 108i allows different circuits 109i to be selected to receive Imax and Imin produced by the current sources 106a/b. Preferably, each of the different circuits 109i has a different current-to-voltage (I-V) characteristic, and three different circuits 109i are shown in FIG. 11C. A first of the circuits 109L comprises a resistor, whose current IL is linearly proportional to the voltage across it: IL~kV, where k equals the conductance of the resistor (1/R). A second of the circuits 109S comprises a MOS diode, which can be formed as shown by connecting the drain of a MOS transistor to its gate. As is known, the current flowing through this MOS diode, IS, is proportional to the square of the voltage across it: IS~k$(V-Vt)^2$, where k is a constant, and Vt comprises the threshold voltage of the MOS transistor. A third of the circuits 109E comprises a p-n diode, which can be formed in one example by connecting the collector of a bipolar junction transistor to its base. As is known, the current flowing through this p-n diode, IE, is exponentially proportional to voltage V across it: IE~$m*e^{n*V}$, where m and n are constants.

Any of these circuits 109L, 109S, and 109E can be selected for use within the I-V selection blocks 108i by closing switches 111L, 111S, 111E in series with each. These switches are respectively controlled by control signals L (linear), S (square), and E (exponential), which together comprise function select signals. These function select signals are issued by the control circuitry 40, and in the example shown, different function select signals a, b, and c are used to control the selection of the circuit 109i in I-V selection block 108a, I-V selection block 108b, and a third I-V selection block 108c appearing in the output stage 104, which will be discussed later. Preferably, but not necessarily, the control circuitry 40 in response to the selection made at aspect 202 would select the same circuit 109i in each of the I-V selection blocks 108a, 108b, and 108c. In this regard, and although not shown, the control circuitry 40 may issue only one set of function control signals—i.e., one set of L, S, and E control signals—which would be received by each of the I-V selection blocks 108a, 108b, and 108c.

In biasing stage 102a, Imax, as provided by aspect 204 in GUI 200, is provided to the selected circuit 109i within I-V selection block 108a, which in turn produces a voltage Vmax as governed by the I-V characteristics of the selected circuit. For example, if resistor 109L is selected, Vmax will equal Imax*R. If MOS diode 109S is selected, Vmax would be proportional to SQRT(Imax). If p-n diode 109E is selected, Vmax would be proportional to the ln(Imax). Vmax is provided to a voltage follower 110a to produce a buffered version of Vmax at its output. Biasing stage 102b is similar, with Imin (204) provided to the selected circuit 109i within I-V selection block 108b, which in turn produces a voltage Vmin as governed by the I-V characteristics of the selected circuit. Vmin is provided to a voltage follower 110b to produce a buffered version of Vmin at its output.

Vmax and Vmin as buffered are provided to a resistance block 112 in the input stage 101, which is controlled by the digital amplitude bus <A> to produce a voltage V(A) that varies with the amplitude value A carried by the bus. V(A) scales linearly with the amplitude values A between Vmin and Vmax, as explained in the '798 Publication.

V(A) is provided to the output stage 104 of the NDAC 100. Specifically, V(A) is provided to a non-inverting input of an operational amplifier (op amp) 114, whose output is provided to the gate of an output transistor 116. The inverting input of the op amp 114 is connected to the top of I-V selection block 108c. Feedback will force the output transistor 116 on to an extent necessary to cause the voltages at the op amp's inputs to be the same; hence V(A) will be dropped across I-V selection block 108c. This voltage drop V(A) induces a current Iout through the I-V selection block 108c and the output transistor 116 in accordance with the I-V characteristics of the circuit 109i (FIG. 11C) selected in block 108c. Because V(A) varies between Vmax (established by Imax) and Vmin (established by Imin), Iout will vary with the set I-V characteristic between Imin and Imax, again as explained in the '798 Publication.

Figure 12A:
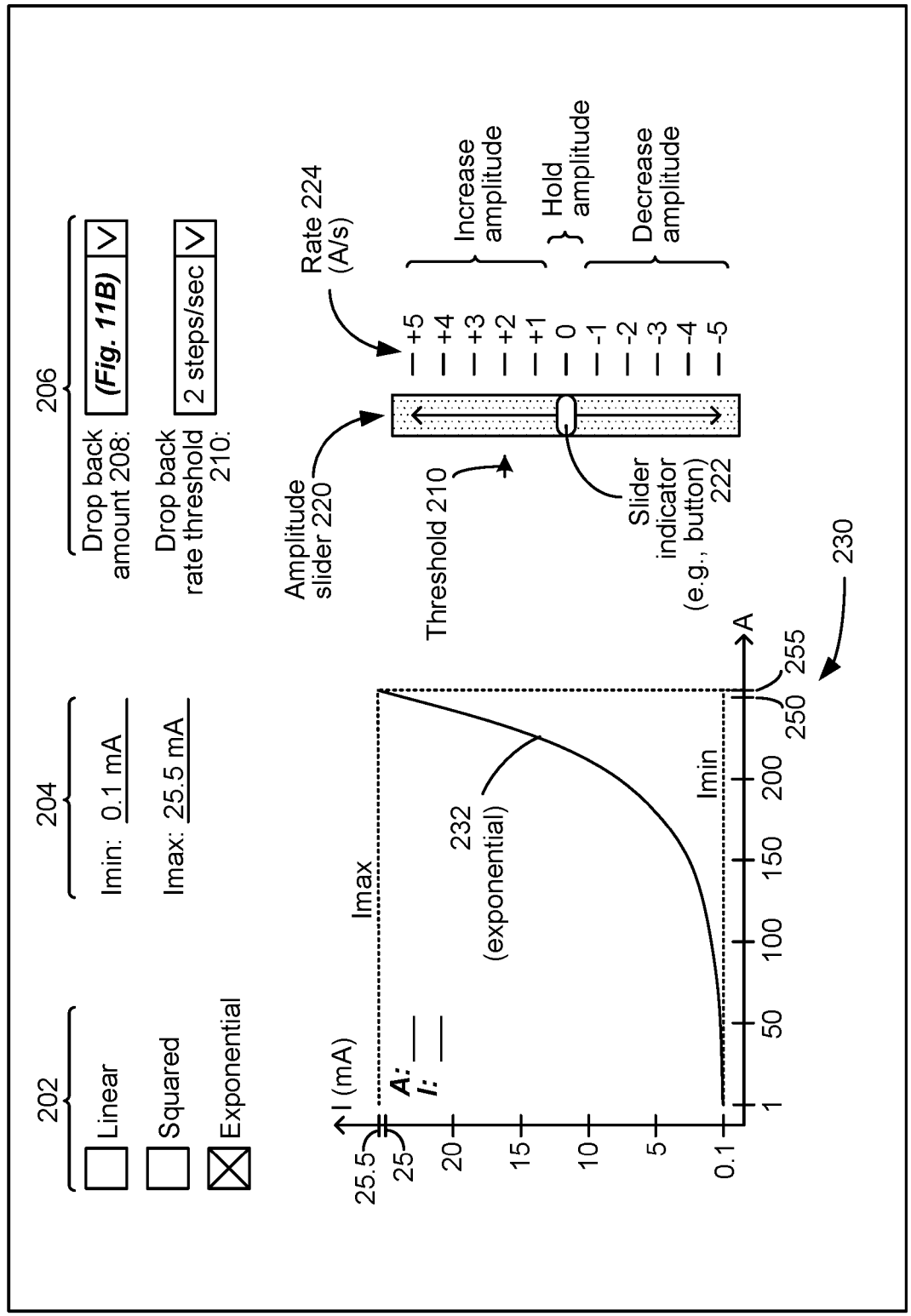

FIG. 12A assumes that the user has selected at aspect 202 that the current magnitude should scale exponentially with the amplitude values, as reflected by relationship 232. The user has also selected that the current magnitude should vary between Imin=0.1 mA and Imax=25.5 mA. As just explained, these selected aspects will be used by the GUI 200 to program the DAC circuitry in the IPG 10. As before, the GUI 200 includes an amplitude slider 220 that can be used to adjust the rate 224 at which the current magnitude will be increased or decreased. If it is assumed as before that the rate 224 specifies a rate at which the amplitude values will be increased, and because the current magnitude in this example varies exponentially with the amplitude values, the current magnitude will also change at an exponential rate. In other words, at a constant rate 224 (e.g., +3), the current magnitude will increase exponentially, and thus will change at a slower rate at lower amplitude values, and at a higher rate at higher amplitude values, which may be advantageous in a given application. That being said, and as mentioned before, the rate 224 may also specify a rate at which the current magnitude will be changed. In this example, at a constant current-magnitude rate 224 (e.g., +1 mA/s), the current magnitude will increase at this constant rate, meaning that the amplitude values would be changed at a logarithmic rate, in accordance with relationship 232.

Figure 12B:
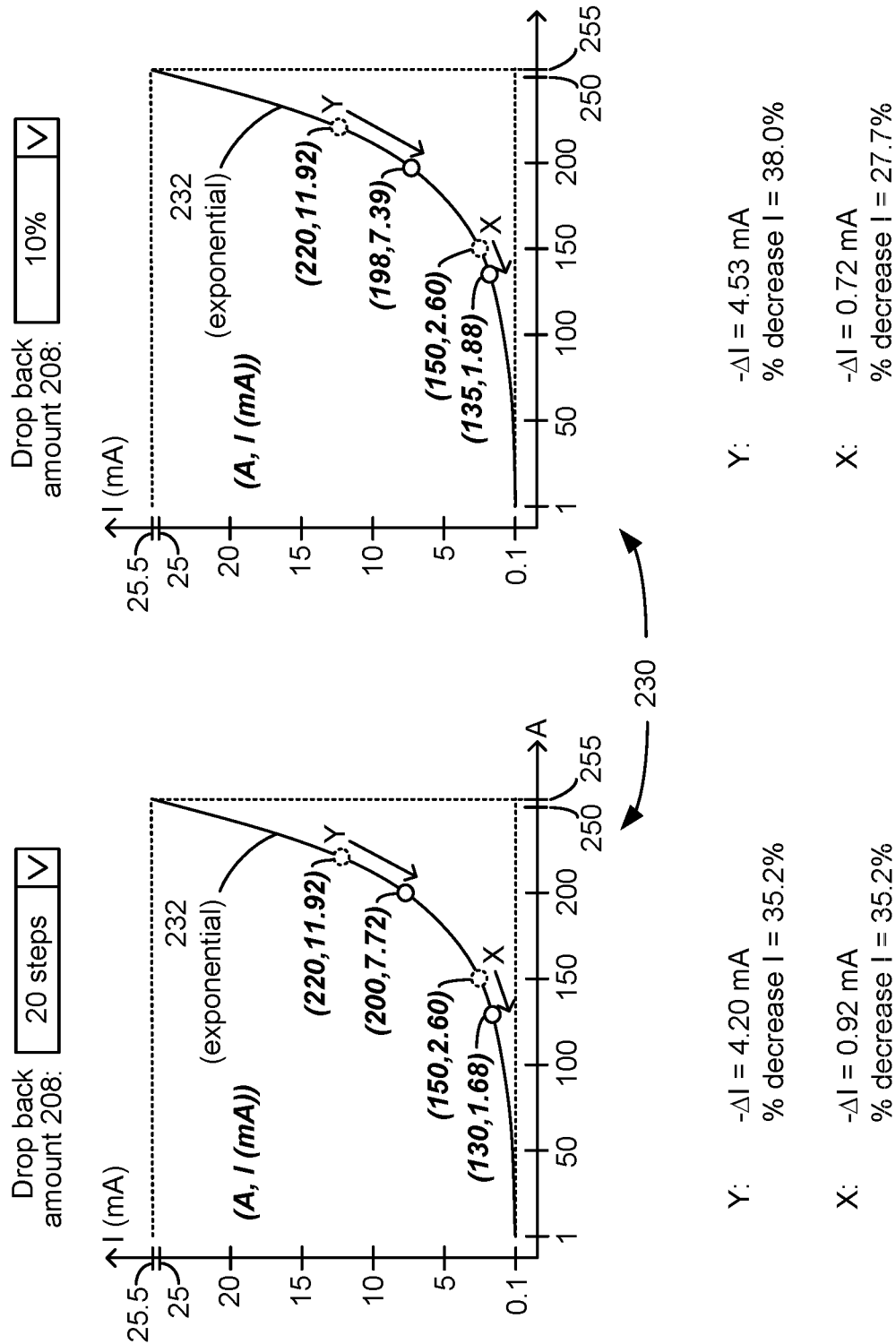
FIG. 12B shows use of different examples of the drop back feature when the exponential relationship is selected.

FIG. 12B illustrates different examples of drop back functionality as applied to exponential relationship 232. Two different drop back amounts 208 are illustrated: a reduction of 20 amplitude values (left), and a reduction of 10% amplitude values. In each, two different scenarios are illustrated: X, where a reduction has occurred at amplitude value 150 (current magnitude 2.60 mA); and Y, where a reduction has occurred at amplitude value 220 (current magnitude 11.92 mA). Although not shown, it is assumed in these scenarios that drop back functionality has been engaged, for example because the rate 224 equals or exceeds the drop back rate threshold 210 when the indicator 222 is released.

When a set reduction of amplitude values is used (left), a larger decrease in the current magnitude is experienced at higher currents (Y; −4.20 mA) than at lower currents (X; −0.92 mA), as would be expected given the exponential nature of relationship 232. Also, as a result of the exponential relationship 232, notice that the percentage reduction in the current magnitude is constant (35.2%), which may be advantageous in a given application. When reduction occurs as a percentage of amplitude values (right), and when compared to a set reduction (left), the reduction is higher at higher currents (Y), and smaller at lower currents (X). This may also be advantageous, as this drop back scenario works a more aggressive reduction of the current at higher currents, which may be favored for safety.

To this point the GUI 200 has been illustrated as useful in controlling, and dropping back, the stimulation parameter of stimulation magnitude (I). However, note that the GUI 200 could also use the same control and interface options to control other stimulation parameters as well, such as pulse width or frequency to name just two examples.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for controlling an implantable stimulator device using an external device, the method comprising:

providing on a screen of the external device a graphical user interface (GUI), wherein the GUI includes an indicator;

receiving at the GUI a first input from a user to control the indicator to adjust a rate at which a current magnitude is increased at one or more of the electrodes;

providing the current magnitude as increased to the implantable stimulator device;

receiving at the GUI a second input from the user to release the indicator; and reducing a present value of the current magnitude at the implantable stimulator device by a set amount if a present value of the rate equals or is above a rate threshold when the indicator is released.

2. The method of claim 1, wherein the implantable stimulator device comprises stimulation circuitry controllable by amplitude values provided by a digital amplitude bus, and wherein present value of the current magnitude is reduced by the set amount by reducing the present amplitude value by a set amount.

3. The method of claim 2, wherein the set amount the present amplitude value is reduced comprises a percentage reduction in the present amplitude value.

4. The method of claim 2, wherein the set amount present amplitude value is reduced comprises a number of amplitude value steps.

5. The method of claim 1, wherein reducing the present value of the current magnitude by a set amount does not comprise reducing the present value of the current magnitude to zero.

6. The method of claim 1, wherein reducing the present value of the current magnitude by a set amount comprises reducing the present value of the current magnitude to zero.

7. The method of claim 1, further comprising holding the present value of the current magnitude constant if the present value of the rate is below the rate threshold when the indicator is released.

8. The method of claim 1, wherein the indicator is configured to be slidable by the user to adjust the rate at which the current magnitude is increased.

9. The method of claim 8, wherein the rate is a function of a length that the indicator is slid.

10. The method of claim 9, wherein the indicator is configured to be selected and held by the user to slide the indicator.

11. The method of claim 10, wherein the indicator is configured to be selected and held by the user using a mouse or touch pad associated with the external device.

12. The method of claim 10, wherein the screen comprises a touch screen, and wherein the indicator is configured to be selected and held by a finger of the user on the screen.

13. The method of claim 1, wherein the present value of the current magnitude is held constant when the indicator is at a zero position.

14. The method of claim 1, wherein releasing the indicator sets the rate to zero.

15. The method of claim 1, further comprising displaying the present value of the current magnitude on the screen.

16. The method of claim 1, wherein the implantable stimulator device comprises stimulation circuitry controllable by amplitude values provided by a digital amplitude bus, and wherein the indicator adjusts the rate at which the current magnitude is increased by adjusting a rate at which the amplitude values are increased.

17. The method of claim 16, further comprising displaying a graph of a relationship that dictates how the current magnitude varies as a function of the amplitude values.

18. The method of claim 17, further comprising displaying a present value of the current magnitude on the graph.

19. A system, comprising:
an implantable stimulator device comprising a plurality of electrodes configured to provide stimulation to a patient's tissue; and
an external device configured to program the implantable stimulator device, the external device comprising:
a screen, and
control circuitry programmed with software, wherein the software when executed is configured to render a graphical user interface (GUI) on the screen, wherein the GUI includes an indicator controllable to adjust a rate at which a current magnitude is increased at one or more of the electrodes when the indicator is selected by a user,
wherein the GUI further comprises a rate threshold, wherein the GUI is configured when the indicator is released by the user to reduce a present value of the current magnitude by a set amount if a present value of the rate equals or is above the rate threshold,
wherein the control circuitry is configured to provide the current magnitude as adjusted and reduced to the implantable stimulator device.

20. An external device configured to program an implantable stimulator device having a plurality of electrodes configured to provide stimulation to a patient's tissue, the external device comprising:
an indicator controllable by user to adjust a rate at which a current magnitude is increased at one or more of the electrodes, wherein the external device is programmed with a rate threshold, wherein the external device is configured when the indicator is released by the user to reduce a present value of the current magnitude by a set amount if a present value of the rate equals or is above the rate threshold; and
control circuitry configured to provide the current magnitude as adjusted and reduced to the implantable stimulator device.

* * * * *